(12) United States Patent
Strauss et al.

(10) Patent No.: US 9,107,571 B2
(45) Date of Patent: Aug. 18, 2015

(54) ECG ACQUISITION AND TREATMENT-RESPONSE SYSTEM FOR TREATING ABNORMAL CARDIAC FUNCTION

(71) Applicant: CARDIMETRIX, LLC, Teaneck, NJ (US)

(72) Inventors: Benjamin Jordan Strauss, Teaneck, NJ (US); Kalman Katlowitz, New York, NY (US); Eric Forkosh, Woodmere, NY (US)

(73) Assignee: CARDIMETRIX, LLC, Teaneck, NJ (US)

( * ) Notice: Subject to any disclaimer, the term of this patent is extended or adjusted under 35 U.S.C. 154(b) by 0 days.

(21) Appl. No.: 13/869,623

(22) Filed: Apr. 24, 2013

(65) Prior Publication Data

US 2013/0281816 A1    Oct. 24, 2013

Related U.S. Application Data

(60) Provisional application No. 61/637,737, filed on Apr. 24, 2012.

(51) Int. Cl.
*A61B 5/04* (2006.01)
*A61B 5/00* (2006.01)
(Continued)

(52) U.S. Cl.
CPC ............. *A61B 5/0006* (2013.01); *A61B 5/002* (2013.01); *A61B 5/0022* (2013.01);
(Continued)

(58) Field of Classification Search
CPC ... A61B 5/1118; A61B 5/0022; A61B 5/7475
See application file for complete search history.

(56) References Cited

U.S. PATENT DOCUMENTS 5,087,243 A   2/1992  Avital
5,269,301 A   12/1993 Cohen
(Continued)

FOREIGN PATENT DOCUMENTS

EP   1720446   11/2006
EP   2226083   9/2010
(Continued)

OTHER PUBLICATIONS

PCT International Application No. PCT/US2013/038052, International Search Report and Written Opinion dated Aug. 23, 2013.
(Continued)

*Primary Examiner* — Christopher D Koharski
*Assistant Examiner* — Philip Edwards
(74) *Attorney, Agent, or Firm* — Barnes & Thornburg LLP

(57) ABSTRACT

A method and system for detecting and treating abnormal cardiac function. The patient's cardiac activity is substantially continuously monitored via a portable wearable device having electrodes and a microcontroller. Features in the monitored cardiac activity indicative of abnormal cardiac function are automatically detected. In response to the detection of an abnormal detected cardiac function, at least one person is automatically alerted of the detected abnormal cardiac function of the patient, and medication may be automatically caused to be administered to the patient. The portable wearable device preferably includes a plurality of electrodes and a microcontroller in communication with the electrodes, adapted to receive sensed cardiac activity signals and create digital signals enabling identification of at least one cardiac parameter. A remote computer server is in communication with the portable wearable device and compares values of the identified cardiac parameter with a range of normal values for the cardiac parameter.

14 Claims, 27 Drawing Sheets

(51) Int. Cl.
*A61B 5/0402* (2006.01)
*A61B 5/0408* (2006.01)
*A61B 5/0456* (2006.01)

(52) U.S. Cl.
CPC .......... *A61B 5/0402* (2013.01); *A61B 5/04012* (2013.01); *A61B 5/4839* (2013.01); *A61B 5/742* (2013.01); *A61B 5/7405* (2013.01); *A61B 5/746* (2013.01); *A61B 5/7455* (2013.01); *A61B 5/0456* (2013.01); *A61B 5/04085* (2013.01); *A61B 5/04087* (2013.01); *A61B 5/6831* (2013.01); *A61B 5/747* (2013.01)

(56) References Cited

U.S. PATENT DOCUMENTS

| | | | |
|---|---|---|---|
| 6,572,542 B1 * | 6/2003 | Houben et al. | 600/300 |
| 8,301,232 B2 | 10/2012 | Albert et al. | |
| 2004/0103001 A1 * | 5/2004 | Mazar et al. | 705/2 |
| 2006/0253301 A1 * | 11/2006 | Simms et al. | 705/2 |
| 2008/0208007 A1 * | 8/2008 | Van Hove et al. | 600/300 |
| 2009/0076336 A1 * | 3/2009 | Mazar et al. | 600/300 |
| 2009/0204013 A1 | 8/2009 | Muhlsteff et al. | |
| 2011/0087115 A1 | 4/2011 | Sackner et al. | |

FOREIGN PATENT DOCUMENTS

| | | |
|---|---|---|
| KR | 10-2010-0005690 A | 1/2010 |
| KR | 10-1065201 B1 | 9/2011 |
| WO | 2005/070289 A1 | 8/2005 |
| WO | 2005070289 A1 | 8/2005 |
| WO | 2011/061733 A1 | 5/2011 |
| WO | 2011061733 A1 | 5/2011 |

OTHER PUBLICATIONS

International Search Report for PCT/US/2013/038052 dated Aug. 23, 2013.

* cited by examiner

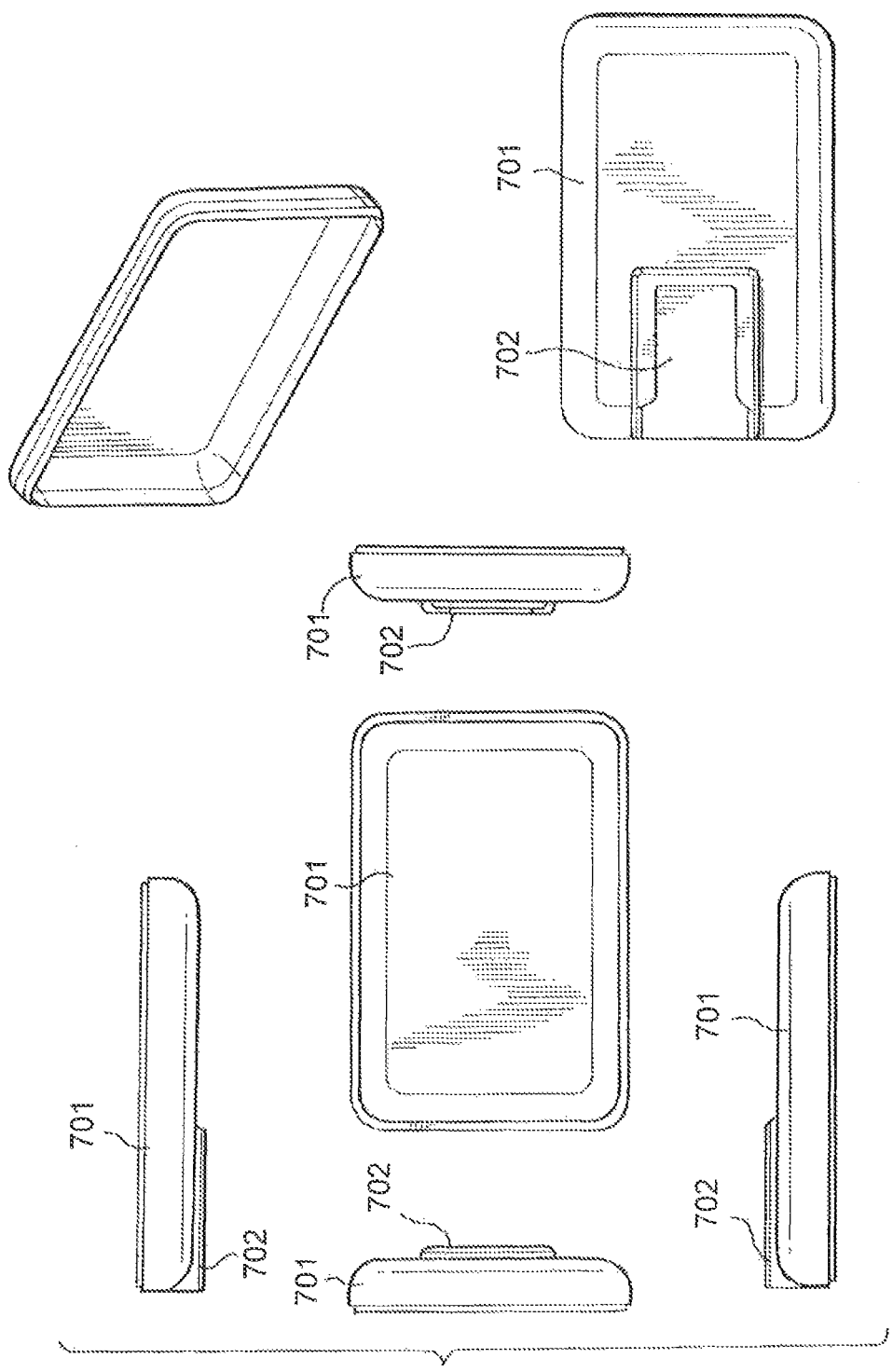

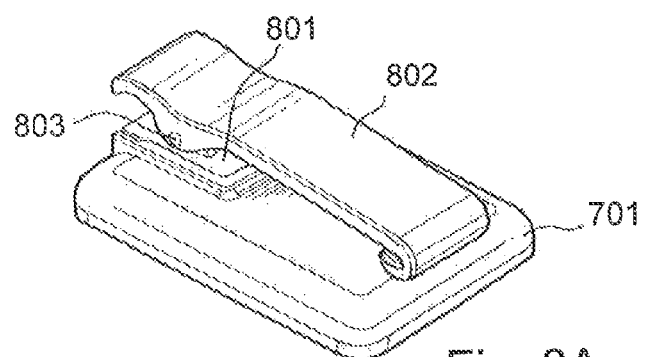
Fig. 8A
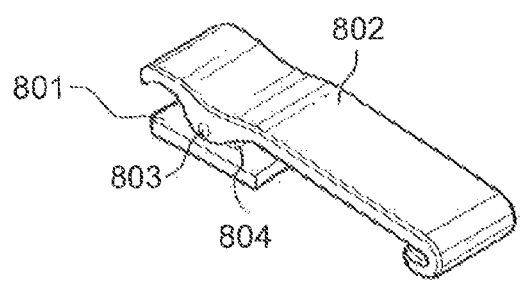
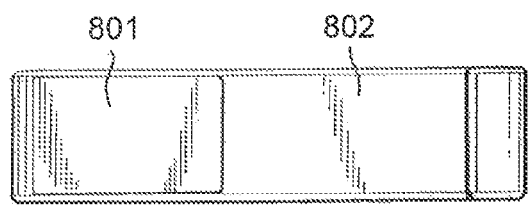
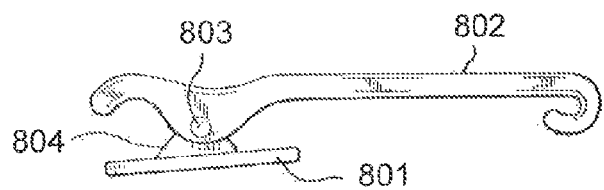
Fig. 8B

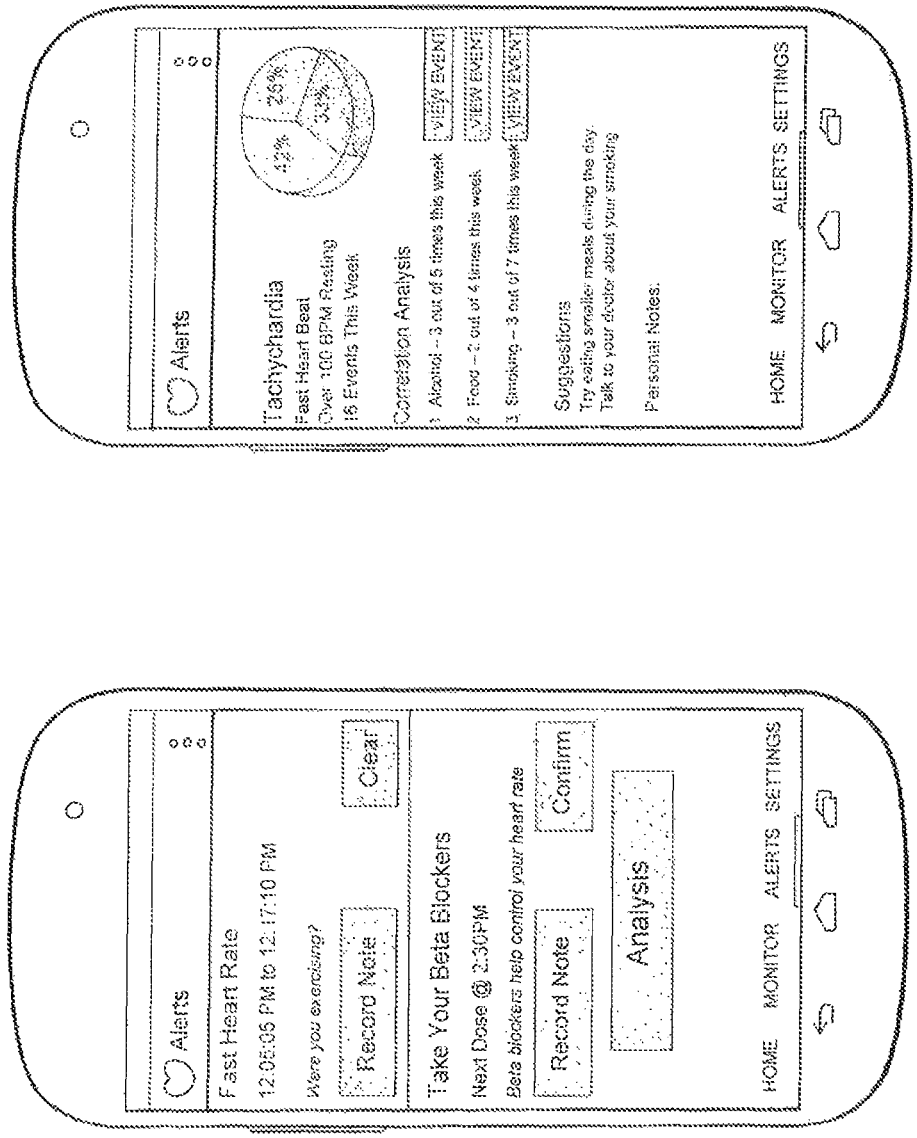

ECG ACQUISITION AND TREATMENT-RESPONSE SYSTEM FOR TREATING ABNORMAL CARDIAC FUNCTION

RELATED APPLICATIONS

Priority is claimed from U.S. Provisional Patent Application No. 61/637,737, filed Apr. 24, 2012, entitled "ECG Acquisition and Treatment-Response System for Treating Myocardial Ischemia", the teachings of which are incorporated by reference herein.

BACKGROUND OF THE INVENTION

1. Field of the Invention

The invention is directed to the interpretation of ECG characteristics in determining the presence of arrhythmia or any other abnormal ECG presentation (including ST segment deviation), a personalized system to improve user feedback, and automated treatment with the delivery of medication.

2. Description of Related Art

Coronary Artery Disease (CAD) is a condition in which the coronary arteries (the blood vessels which supply the myocardium with oxygenated blood) accumulate plaque, and become less effective in delivering oxygenated blood to the heart. CAD is the most common cause of death worldwide. CAD causes periods of myocardial ischemia, in which the heart's oxygen demand is greater than the supply delivered to it. Prolonged periods of myocardial ischemia lead to necrosis of cardiac cells, resulting in myocardial infarction (MI), commonly known as a heart attack. Acute silent myocardial ischemia is an episodic condition in which blood flow to the heart is restricted, causing a deficiency in oxygen supply to the myocardial tissue and potentially leading to myocardial infarction without demonstrating any symptoms. Whereas non silent myocardial ischemia presents with angina pectoris (a tight pain in the chest) that makes the patient aware of the condition, silent ischemia provides no indication for the victim to obtain immediate treatment. Further, angina pectoris is not a reliable indicator of myocardial ischemia, as patients have varying thresholds for what they consider to be painful sensations of angina. Additionally, the sensations of angina pectoris have been proven to start minutes after myocardial ischemia has started, not be present in many cases of myocardial ischemia, and end significantly before and episode of myocardial ischemia ends.

Almost all patients who experience myocardial ischemia accompanied by angina pectoris also experience silent episodes of myocardial ischemia. Furthermore, there are many patients who experience exclusively silent episodes of myocardial ischemia. The American Heart Association estimates that between 3 and 4 million Americans experience episodes of silent ischemia. Risk factors for silent ischemia include previous myocardial infarctions, coronary artery disease, diabetes, hypertension, smoking, obesity, and existing cardiomyopathy. Cardiomyopathy due to repeated episodes of silent ischemia is one of the most common causes of heart failure in the US. In addition to being a precursor to myocardial infarction, active ischemia is a common underlying cause of ventricular arrhythmia and sudden cardiac death. Additionally, another arrhythmia known as atrial fibrillation can also present without symptoms and is a severe public health burden, as it is a major risk factor for Cerbrovascular Accidents, also known as strokes.

Silent Ischemia can be accurately diagnosed by electrocardiogram, most specifically via transient ST segment changes, T wave inversions, and an increase in heart rate. ST segment depression is the most reliable electrophysiological indicator of acute myocardial ischemia. Nitrates, beta blockers, and calcium channel blockers dilate the coronary arteries and contribute to balancing the heart's oxygen supply and demand. They are the common pharmacological treatment options for ischemia. Nitrates can be administered sublingually by the patient, but is only realistic when indicative symptoms are present. Long-term transdermal nitrate patches can be used prophylactically, but are inevitably subject to the body building a tolerance from extended periods of administration, and must not be worn more than approximately 50 percent of the time. Furthermore, due to the longer time of onset via this route (30-60 minutes) this route of delivery cannot treat an acute onset. Daily beta blocker and calcium channel blocker pills can also prevent or relieve ischemia, but bear the burden of daily side effects that often cause patients to stop taking them.

Thus, there exists a deficiency in the common treatment methods, insofar as the patient can only treat himself/herself during myocardial ischemic episodes in which he feels the sensations of angina pectoris, but not when the attacks are silent. Further deficiencies in the current treatment methods are the necessity to remove a nitrate patch for a substantial portion of time, to minimize nitrate tolerance, thus leaving the patient vulnerable to ischemia attacks during those periods. There exists no system for automated delivery of treatment for myocardial ischemia based on detection of the indicative physiological changes.

SUMMARY OF THE INVENTION

The above and other problems are solved by the invention, which is a device/system that monitors a patient's ECG, detects clinically significant deviations from a normal ECG, and may optinally also automatically deliver doses of medication. ECG electrodes are aligned in a wearable form factor. The wires are connected to signal acquisition and processing hardware, which removes the interfering and destructive signals from the desired signal. This hardware is interfaced with a microcontroller. Embedded on the microcontroller is an algorithm for detecting the level of the ST segment (normal, depressed, elevated). Embedded on the microcontroller is also an algorithm for automatically administering a medication of the treating party's choice, with treatment specifications and criteria predetermined by the treating party. Because ST segment elevation is indicative of an acute onset myocardial infarction that requires immediate advanced medical care, the microcontroller is interfaced with a speaker/ alarm that alerts the wearer to consult a medical authority. The signal acquisition hardware, the microcontroller, the linear actuator, and the medication containing component are all housed in a unit that can be worn on the belt like a pager.

The invention also preferably includes two buttons, in different locations, on the exterior of the device casing that a patient pushes simultaneously when he wants to self-medicate. The buttons must be pressed for a predetermined period of time, for example between 3 and 10 seconds. These parameters are to prevent unintended medicating due to unintentional pushing of the buttons. Upon delivery of a self-medicating dose, the unit disables both self-administering and automated delivery for a predetermined amount of time, so as to prevent overdosing. There is an LED on the exterior of the device that flashes different colors to indicate low battery, current dosing in process/myocardial ischemia detected, and ST elevation detected. Quantity of, intervals between, and ECG samples from, and levels of ST segment can be stored for eventual examination by a treating party.

When administration of liquid medication is indicated, a linear actuator pushes a plunger through the bottom, upwards through a medication container. At the top of the medication container is a rubber top. The tubing connects to the top and of the medication container, and has a sharp tip with which to puncture the rubber, so as to create a pathway through which the medication can flow upon actuation. The medication progresses through, and to the other end of the tubing. At this end of the tubing is a conduit into the body, at an anatomical location of the treating party's choice. This conduit, either a subcutaneous needle, or a micro-needle patch, is kept in place, and stabilized by an adhesive sticker. If placed on the lower part of the abdomen, and the treating party desires the use of a grounding electrode, the grounding electrode and medication conduit can be placed on the same adhesive sticker.

The invention also includes a method for detecting and treating abnormal cardiac function in a mammalian patient. A mammalian patient's cardiac activity is substantially continuously monitored via a portable wearable device having electrodes and a microcontroller in communication with the electrodes. Features and/or parameters in the monitored cardiac activity indicative of abnormal cardiac function are automatically detected. In response to an abnormal detected cardiac function in the detecting step, at least one person of the detected abnormal cardiac function of the patient is automatically alerted. Optionally, upon detecting abnormal cardiac function, data from the patient is requested concerning ordinary patient activity that corresponds to the detected abnormal cardiac function. Preferably, the automatically alerting step includes the step of alerting the patient on the patient's communication device. Preferably, in the case of abnormal heart rate, the automatically alerting step includes the step of alerting the patient on the patient's communication device via local connection between the portable wearable device and the communication device. The automatically alerting step may also include the step of alerting a remote healthcare practitioner via local connection between the portable wearable device and the patient's communication device and thence to the remote healthcare practitioner.

Optionally, the inventive method also includes the step of causing to be administered at least one medication corresponding to the detected abnormal cardiac function. Where the patient is human, the automatic medication administration step may include the step of alerting the patient to self-administer the at least one medication; such alert may entail i) sending a message to the patient's communication device or ii) causing the portable/wearable device to emit a human-perceivable message, such as at least one of a sound, a light, a vibration, or a change in temperature of an element of the portable wearable device. Where the patient is non-human, the automatic medication administration step may include the step of alerting a nearby human to administer the at least one medication to the patient, either by sending a message to the nearby human's communication device, causing the portable wearable device to emit a human-perceivable message, or the like. In addition or in the alternative, the automatic medication administration step may also include the step of administering the at least one medication via the portable wearable device.

In the inventive method, the monitoring step may preferably include the steps of attaching electrodes to the patient; detecting cardiac activity via the electrodes; creating signals corresponding to the detected cardiac activity, the signals enabling identification of at least one detectable cardiac parameter; and sending the signals to a computer for comparison of a value of the detectable cardiac parameter to a range of normal values for the cardiac parameter. The signal sending step may further include the step of sending the signals from the portable wearable device to a remote computer server via the patient's communication device.

The invention also includes a system for detecting and treating abnormal cardiac function in a mammalian patient. The system includes a portable wearable device, having a plurality of electrodes adherable to the patient's body, the electrodes sensing cardiac activity and creating signals corresponding to the sensed cardiac activity. The portable wearable device also includes a microcontroller in communication with the electrodes, adapted to receive the sensed cardiac activity signals and create digital signals enabling identification of at least one cardiac parameter. A remote computer server having read/write memory is provided in communication with the portable wearable device, the server adapted to compare values of the identified at least one cardiac parameter with a range of normal values for the at least one cardiac parameter stored in the read/write memory.

Preferably, the inventive system also includes a user interface, such as a smartphone application, residing on a local user communication device in local communication with the portable wearable device. The user interface is adapted to enable communication between the portable wearable device and the remote computer server and to receive analysis of the identified at least one cardiac parameter by the remote computer server. The user interface preferably also may accept user-enterable information (e.g., physical activities that may explain abnormal cardiac activity, symptoms being experienced by the user/patient, etc.) and communicate the user-enterable information to the remote computer server. The at least one cardiac parameter detectable/identifiable may include at least one of P, Q, R, S, T, and U waves.

Preferably, the inventive system also includes a practitioner interface, residing on a healthcare practitioner's device (e.g., practitioner's smartphone or computer, or a website accessible thereby) in communication with the remote computer server, adapted to enable a healthcare practitioner to review the identified at least one cardiac parameter.

Optionally, the portable wearable device may include a medication dispensing module having a dispensing mechanism and a quantity of at least one medication. When the remote computer server determines that the identified at least one cardiac parameter is not within a normal range, the remote computer server communicates an instruction to the portable wearable device to dispense a dose of the medication.

BRIEF DESCRIPTION OF THE DRAWINGS

FIG. 7 Battery pack casing, which serves as back casing for device, in accordance with one embodiment of the invention.

FIG. 8a belt clip locking into channel on back of battery pack casing, in accordance with one embodiment of the invention.

FIG. 8b belt clip connected to plate in accordance with one embodiment of the invention.

DETAILED DESCRIPTION OF THE INVENTION

Description will now be given with reference to the attached FIGS. 1-24. It should be understood that these figures are exemplary in nature and in no way serve to limit the scope of the invention, which is defined by the claims appearing hereinbelow.

Figure 1A:
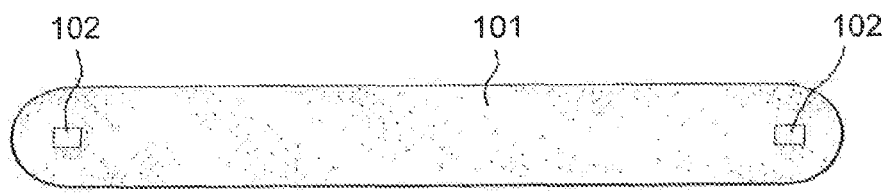
FIG. 1a Electrode adhesive patch, to be worn on skin in accordance with an embodiment of the invention.
Figure 1B:
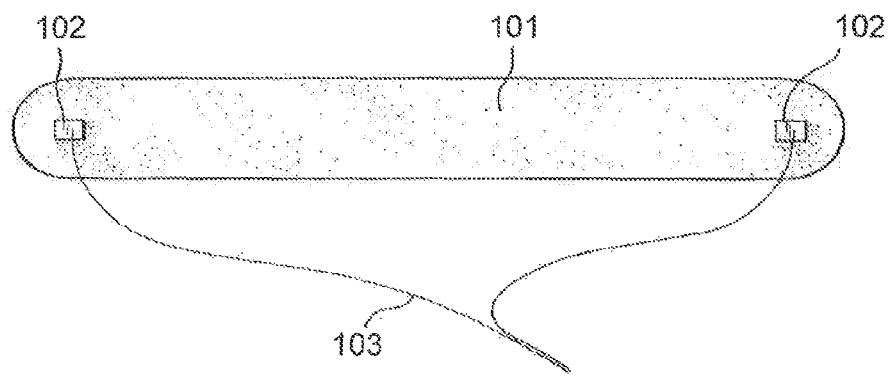
FIG. 1b Electrode wires attached to electrode adhesive patch in accordance with an embodiment of the invention.
Figure 2:
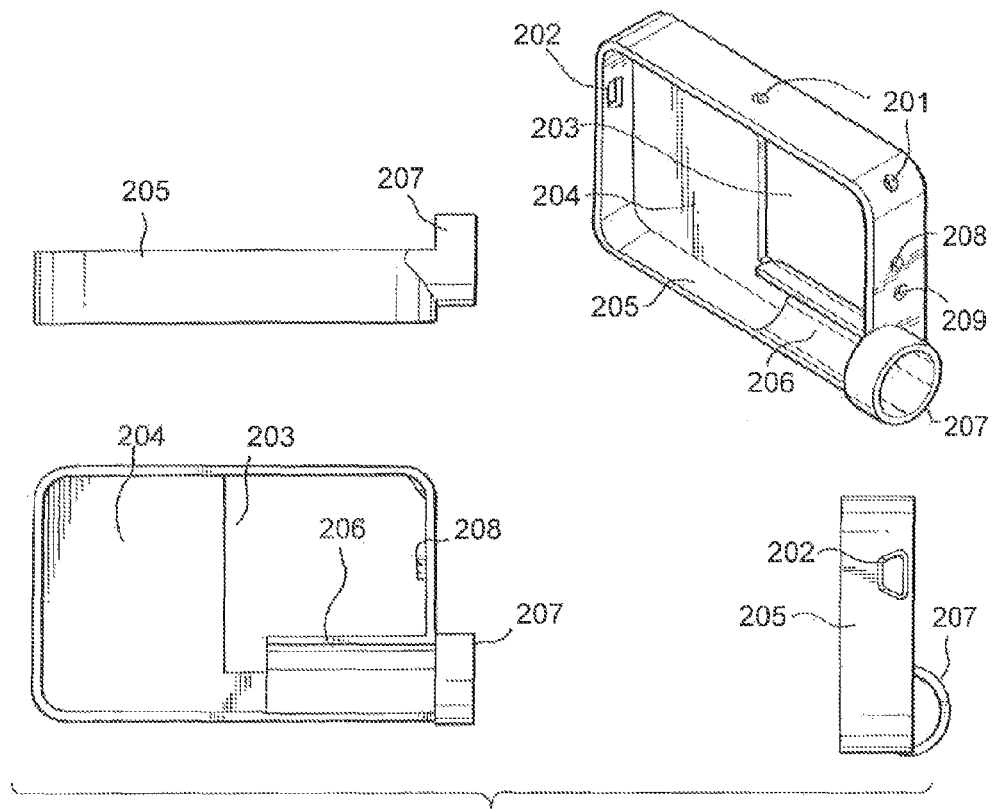
FIG. 2 Middle casing for a device in accordance with one embodiment of the invention, which houses the signal acquisition and processing hardware, the H bridge, the microcontroller, the linear actuator.
Figure 4:
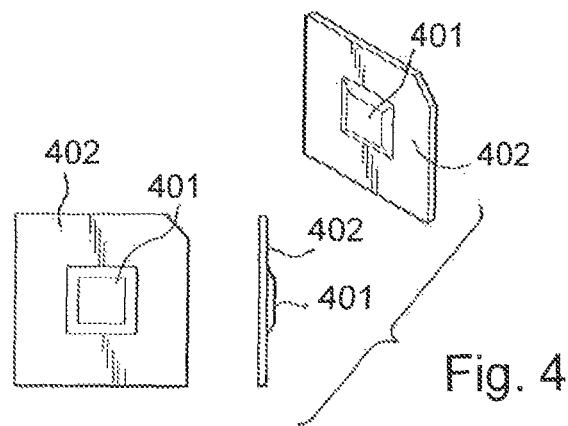
FIG. 4 Signal acquisition and processing hardware in accordance with one embodiment of the invention.
Figure 5:
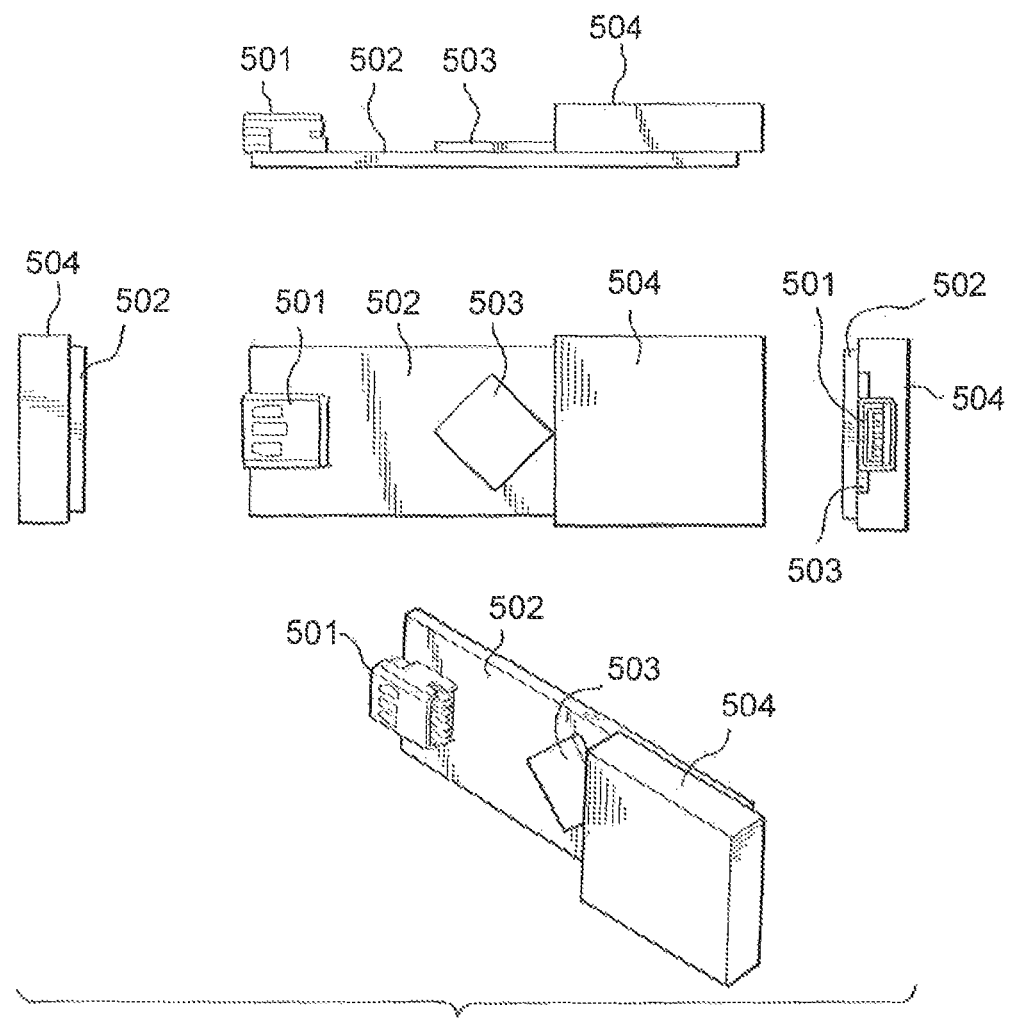
FIG. 5 Microcontroller board (e.g., Teensy 2.0++) in accordance with one embodiment of the invention.
Figure 6:
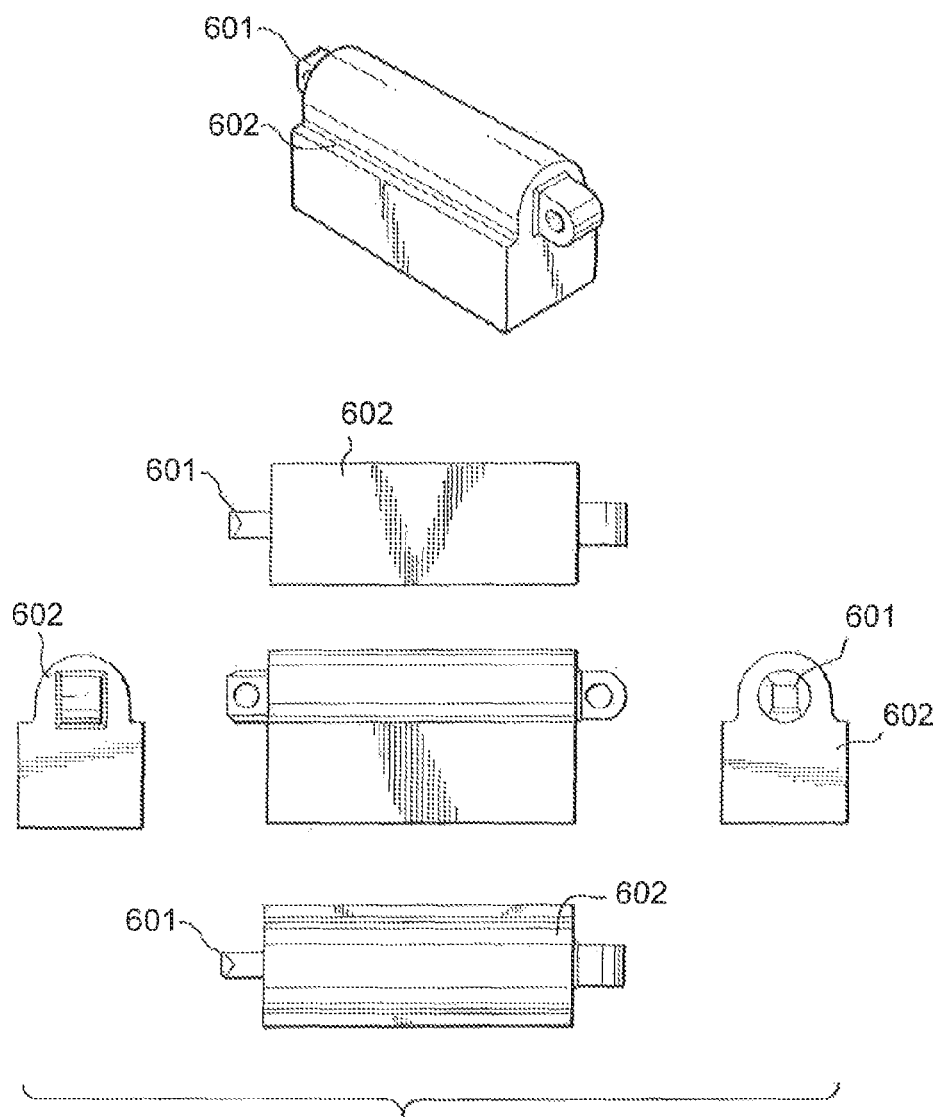
FIG. 6 Linear Actuator (e.g., Firgelli PQ12) for actuating medication, held in its container, through tubing, in accordance with one embodiment of the invention.

The device of one embodiment of the invention includes an electrode adhesive strip (FIGS. 1a, 1b), comprising a strip that adheres to the skin (101) and two electrodes (102) for the acquiring an ECG signal. The entirety of the strip (101) contains a layer of adhesive on it, so as to ensure adhesion to the body with minimal deviation from the site of application. These electrodes (102) are connected by wires (103), which pass through a hole (209) in the siding (205) of the device middle casing, to signal acquisition and processing hardware (FIG. 4). The signal acquisition and processing hardware consists of a printed circuit board (PCB) (402) connected to the TI ADS 1298 signal acquisition and processing device (401), via a hole through the middle casing of the device (28), as shown in FIG. 2. Held in the device middle casing (FIG. 2), secured to its back in the upper left region (203) is the TI ADS 1298 signal acquisition and processing hardware, as well as a microcontroller (502) connected to an H-bridge (504) (FIG. 5), piezoelectric buzzing device (1205), an LED (FIG. 1105), linear actuator (FIG. 6) (601, 602), and attached to the back of the middle casing (204) is a battery pack casing (FIG. 7) (701). The battery pack casing (701) contains a channel on its back (702) that locks with the plate in (FIGS. 8a, 8b) (801) of the belt clip (802) which can be used to wear the device on a belt.

Figure 9:
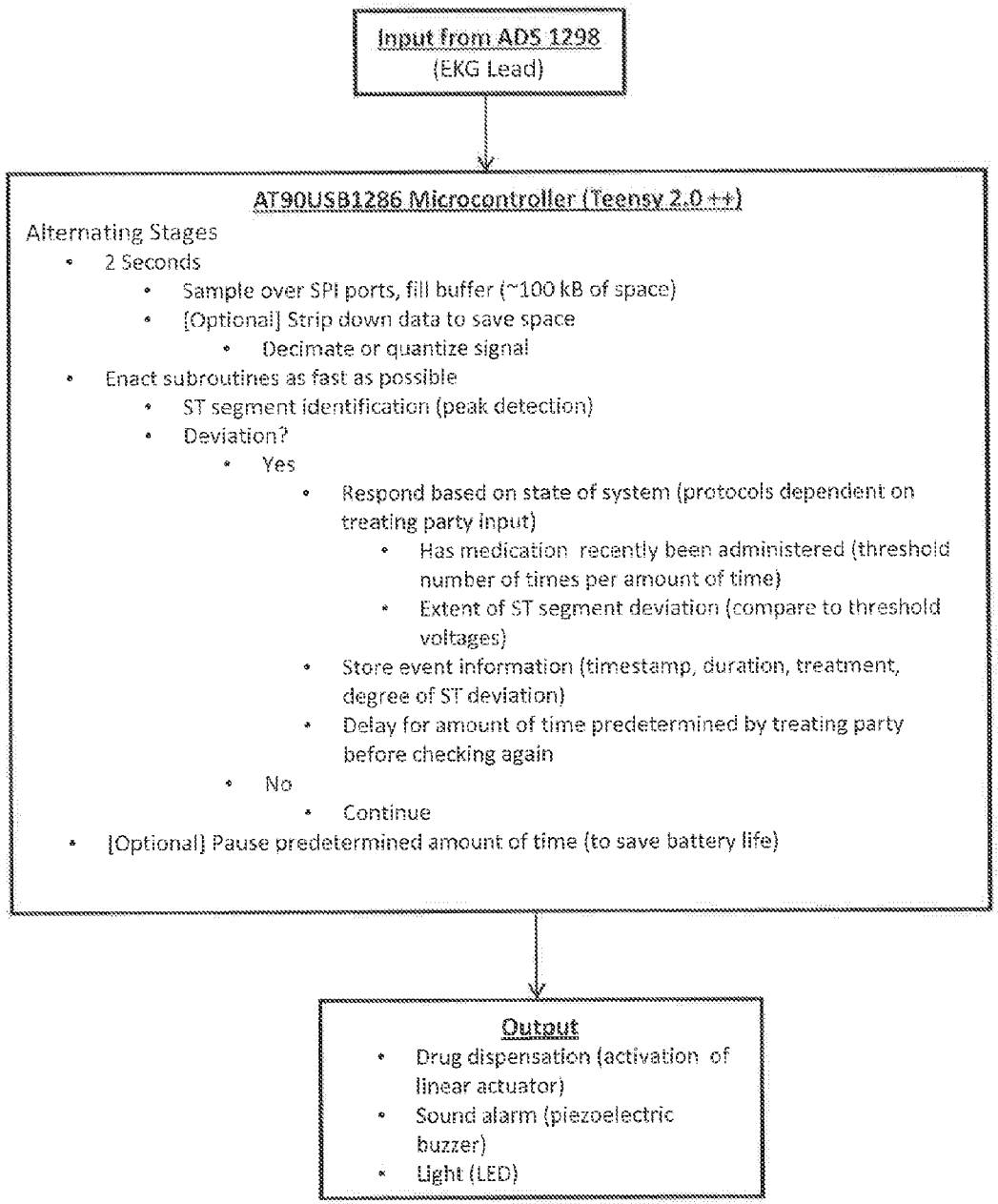
FIG. 9 Code Flow Chart, which serves as the algorithm for detecting ST segment changes on ECG, and for the administration of medication, in accordance with one embodiment of the invention.
Figure 10:
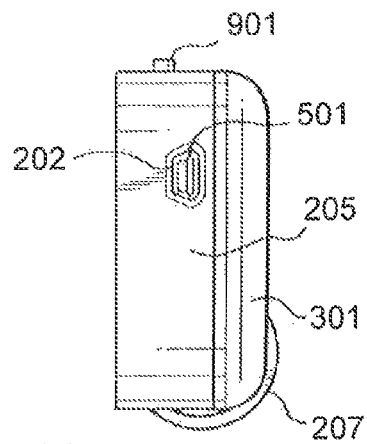
FIG. 10 Bottom view of front and middle casing for device together in accordance with one embodiment of the invention.
Figure 11:
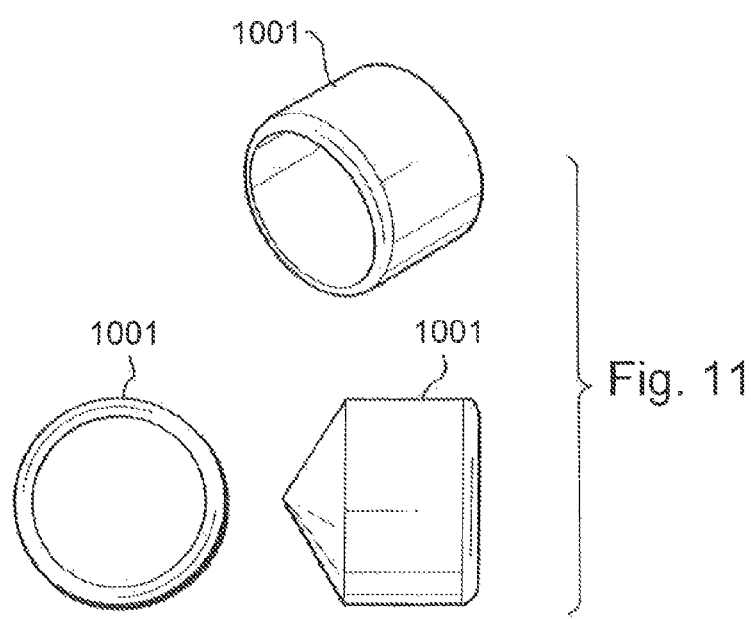
FIG. 11 Rubber plunger bottom that is placed at bottom of medication container in accordance with one embodiment of the invention.
Figure 12:
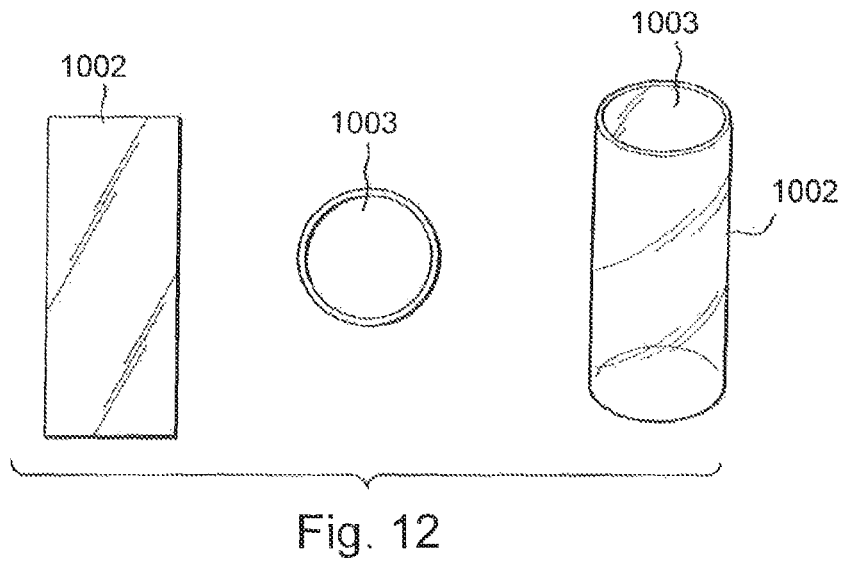
FIG. 12 Medication containing unit in accordance with one embodiment of the invention.
Figure 13:
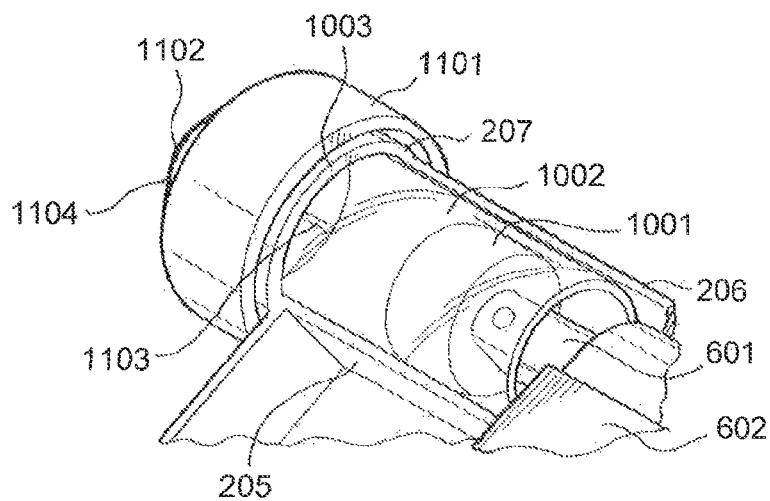
FIG. 13 View of medication containing unit placed and secured inside device in accordance with one embodiment the invention, with linear actuator advancing rubber plunger to deliver medication.

The TI ADS 1298 signal acquisition and processing hardware (401, 402) provides inputs to the microcontroller's processor (503). The algorithm for detection of ischemia, which is specified for the patient by the treating party (FIG. 9), is embedded on the microcontroller unit (502). The treating party can interface the microcontroller of (FIG. 5) with his computer by connecting the two via USB cable, which can be plugged into micro USB connector (501) at the opening at the bottom of the casing (202). A user interface (FIG. 18) on the treating party's computer prompts the treating party, asking for the minimum level of ST segment deviation and duration necessary to administer medication; the length of time before administering additional doses if necessary; what volume of the drug to administer with each administration (distance of actuation); when to alarm patient to seek further medical assistance; at which heart rates ST segment deviation is to be disregarded. These variables are incorporated into the embedded algorithm (FIG. 9). Preferably, the user interface is a graphic user interface (GUI). In addition or in the alternative, preset "packages" of variables may be made available to the treating party so as to minimize the degree of specificity required of the treating party. For example, customizing variables might include gender, weight, blood pressure, age, and other vital statistics. In response to these type of variables populating the algorithm, the algorithm can offer either a recommended dosing regimen or offer the treating party a selection from among a number of treatment options (e.g., conservative, average, or aggressive, which trigger a dosing in response to differing levels of events detected). These and other options in the user interface are contemplated.

Figure 3:
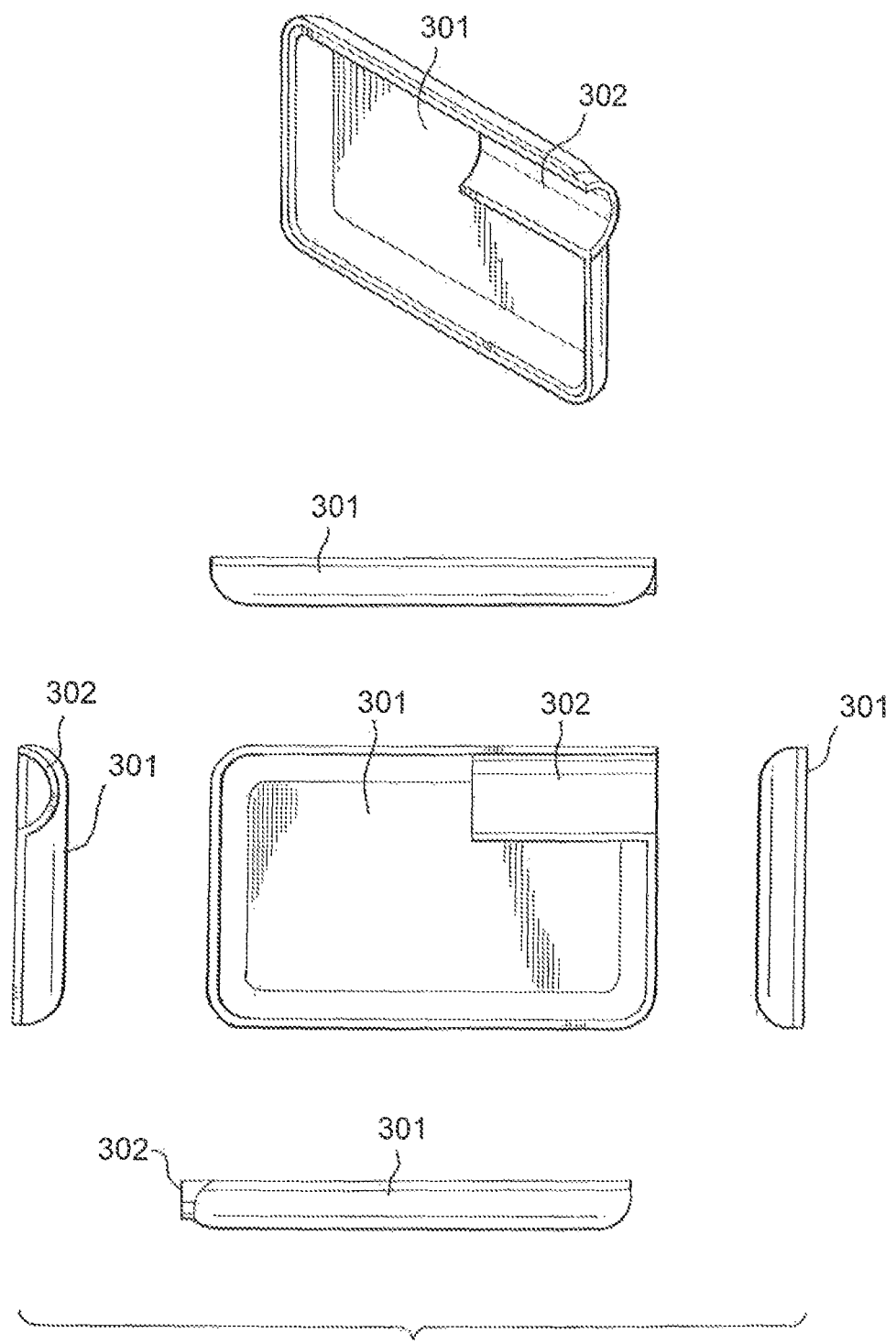
FIG. 3 Front casing for a device in accordance with one embodiment of the invention.

Upon detection of an ST segment that matches the criteria for administration of medication, the microcontroller unit (502, 503) commands the linear actuator unit (FIG. 6) (602) to actuate its rod (601), pushing a piston (FIG. 11) (1001) through its container (FIG. 12) (1002), which is loaded with medication. The container is covered and sealed with a penetrable rubber top (1003). The medication container (1002) is supported and held in placed by a hollow, semi-cylindrical structure (206). It is further supported by an additional semi-cylindrical structure (302) which is attached to the device front casing (301) which is shown in FIG. 3. The top screw-cap (FIG. 14) (1101), which is connected to the bottom screw cap (207), has a hollow, sharp point that pierces through the rubber (1103) as seen in (FIG. 13), and creates a conduit through which medication can flow, into medication tubing, through the needle, micro-needle patch, or other drug introduction system, and into the body. The medication tubing is secured in between two hollow cylinders (1102, 1104) of the top screw-cap (1101).

Figure 14:
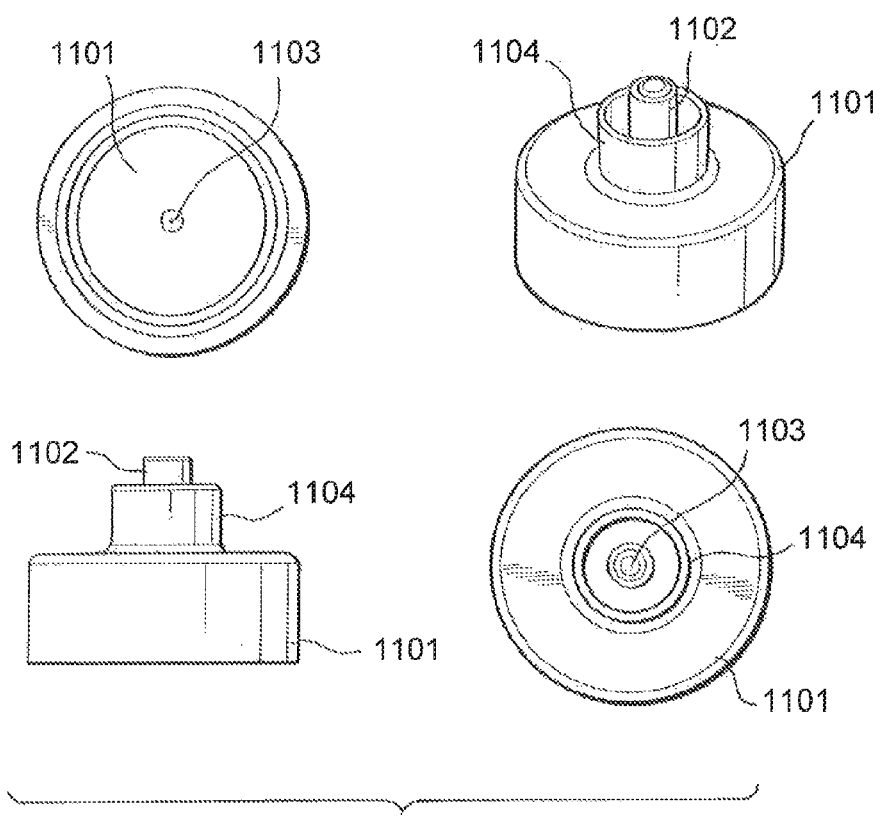
FIG. 14 Screw-cap top in accordance with one embodiment of the invention.
Figure 15:
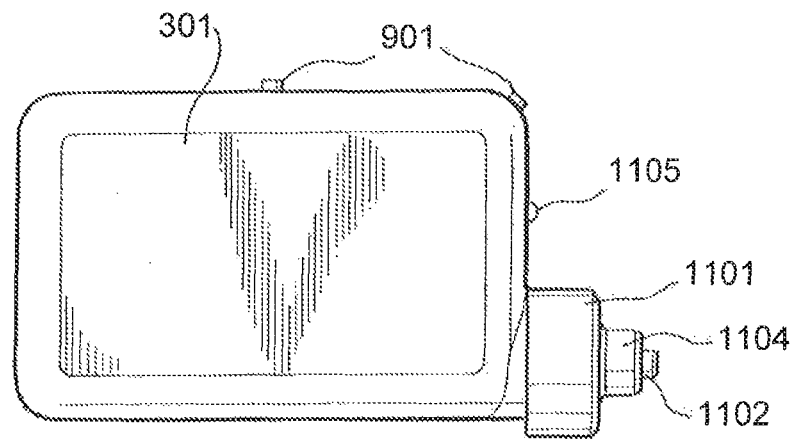
FIG. 15 Front view of assembled device container in accordance with one embodiment of the invention.
Figure 16:
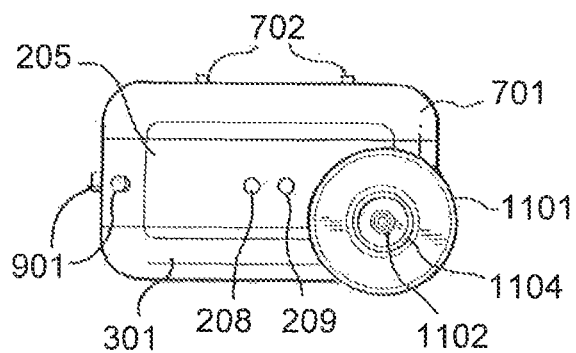
FIG. 16 Top view of device casing in accordance with one embodiment of the invention.
Figure 17:
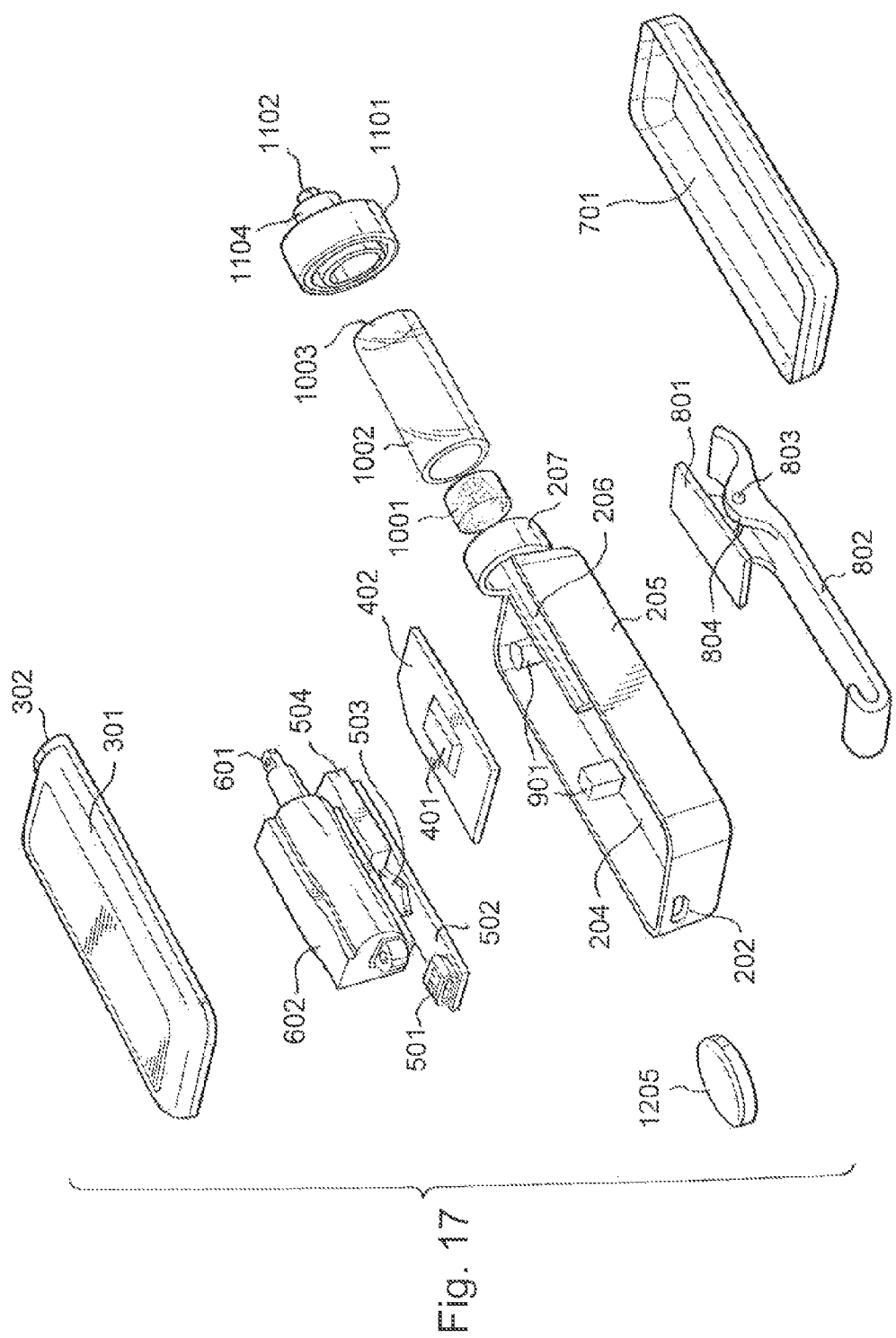
FIG. 17 Exploded view of an entire device in accordance with one embodiment of the invention.
Figure 18:
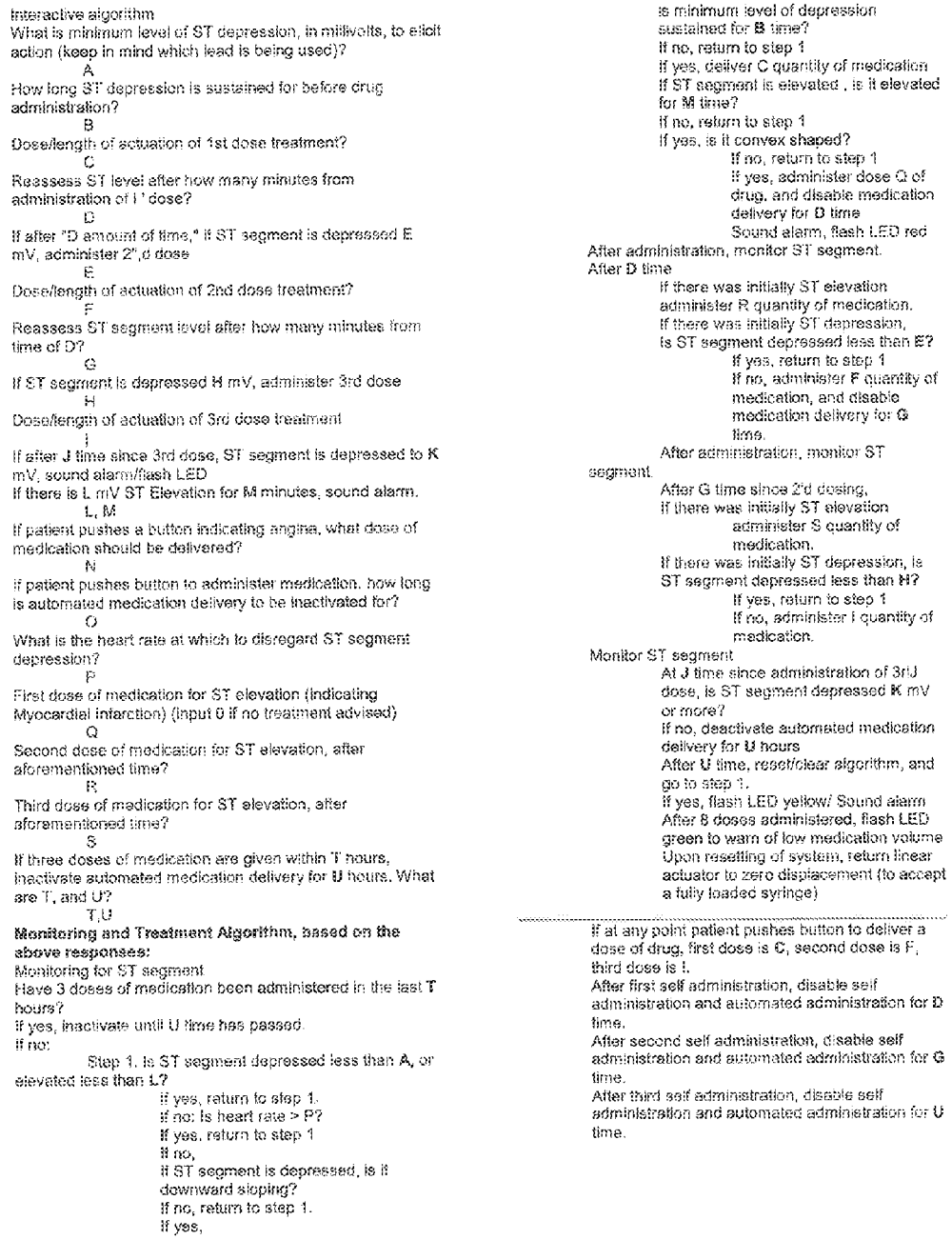
FIG. 18 Interactive user interface for treating party to customize for patient-specific use in accordance with one embodiment of the invention. This user interface serves as the inputs for the detection and treatment systems of FIG. 9.
Figure 19:
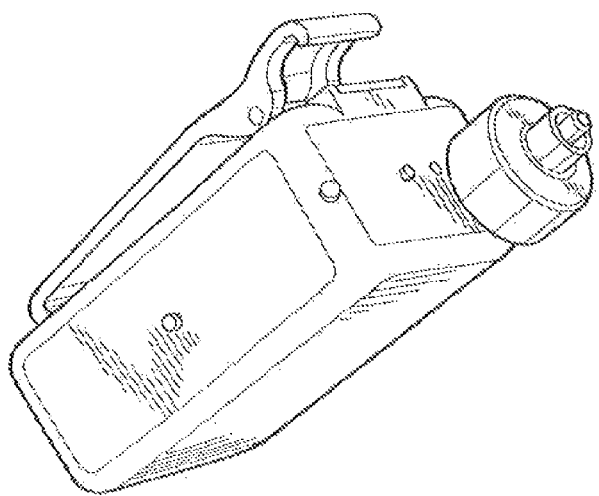
FIG. 19 is a perspective view of an overall device in accordance with one embodiment of the invention.

Medication containers can be replaced by screwing off the top screw-cap (1101) shown in FIG. 14, that is connected to the bottom screw-cap (207), sliding out a medication container, placing in a new one, and resetting the location of the linear actuator rod (601).

After a dose of medication is administered, the device is disabled from delivering medication for a period of time predetermined by the treating party. After that time, if the ST segment still deviates a certain distance from normal (isoelectric line), a second dose is administered. After this dose is administered, the device is disabled from delivering medication for a period of time predetermined by the treating party. After that time, if the ST segment still deviates a certain distance from normal, a third dose is administered. After this dose is administered, the device is disabled from delivering medication for a period of time predetermined by the treating party. During all administration periods, and their subsequent times during which another dose cannot be delivered, an LED (1105) seen in (FIG. 15), which protrudes through a hole in (208) on the side of the device middle casing (205) flashes green, indicating a period of treatment. The LED (1105) is located at the top of the device. When the volume of medication in the container is low, the LED (1105) flashes yellow. When there is ST depression or ST elevation for a prolonged period of time, as specified by the treating party, the LED (1105) flashes red.

After a period of time since administration of the third dose, as determined by the treating party, if the ST segment is still deviated from normal, the LED (1105) flashes red, and the alarm (1205) sounds, indicating the patient must seek further, immediate medical attention.

Upon this detection of ST segment deviation, the timing of the event, the ST segment levels throughout the event, the duration of the event, and the treatments of the event, until the ST segment returns to a normal range, are all recorded and saved for the treating party to examine upon interfacing with his computer.

Should the patient feel chest pain and elect to administer a dose of medication, he may activate the device manually. So as to prevent inadvertent and unintentional self-dosings, it is preferred that more than one button be used for manual self-dosing. As an example, two buttons 901 can be provided. In addition or the alternative, the button(s) (901) may be required to be depressed simultaneously for an extended period of time, e.g., between 3 and 10 seconds, to manually administer the medication. The bottom end of the tubing secures to the device cap that covers the medication containment system. The other end of the tubing is connected to a combination of adhesive and either a subcutaneous needle, micro-needle array patch, or other system which introduces drugs into the body. Optionally, the device may disable manual self-dosing unless a cardiac event is also detected, either simultaneously with the desired dosing or within a predetermined period of time. For example, if no event is detected, the patient will not be able to self-dose so as to prevent inadvertent misconstruction of a different source of discomfort (e.g., a sore muscle) by the patient as a cardiac event. By contrast, if a small event is actually detected that would fall under the preset threshold for automatic dosing and the patient experiences pain, self-dosing will be enabled. These and other options are contemplated.

Thus, the invention provides a device and method for monitoring and analyzing bioelectric (more specific, ECG) signals, and delivering automated therapy based on the analysis. The algorithm customized for patient by treating party. The invention includes a device for detecting, treating, and terminating ischemic episodes of the myocardium. The device has electrodes on a template that adheres to the body, in a region and alignment of choice of the wearer's treating healthcare practitioner. The electrodes acquire an ECG signal, and they are interfaced with a signal acquisition, filtering, and amplifying chip, which acts on the acquired signal. This chip is interfaced with a microcontroller, which has an algorithm embedded on it, with which to analyze and process the ECG signal to determine the presence or absence of myocardial ischemia. Embedded on the microcontroller is an algorithm, that determines, based on the processed ECG signal and the treating party's specifications, the need for delivery of medication. When this need exists, an actuator pushes medication through a vial and tubing, and into the wearer's body. The medication vial, microcontroller, signal acquisition hardware, and actuator systems are contained in a pager-like device that can be worn on a belt.

Another embodiment of the invention is an interactive cardiac monitoring system 1900 as depicted in FIGS. 20-24. Monitoring system 1900 locally detects cardiac activity and transmits signals corresponding to the detected cardiac activity to a remote computer for analysis. The remote computer extracts various features and parameters from the detected cardiac activity and compares them to baseline or normal values for such features and parameters. The analyzed cardiac activity is made available to a remote physician or other healthcare practitioner, e.g., via a website or pushed to a mobile device or the like.

If in the comparison of detected cardiac activity to baseline/normal activity an abnormality is discovered, an alert can be sent to the patient. The alert can be a request for information concerning a possible innocent explanation for the detected abnormality (e.g., elevated heart rate caused by exercise). In addition or in the alternative, it can take the form of instructions to take medicine or to seek medical assistance immediately, or the like. The system is configurable so that an alert can be sent automatically from the remote computer to the patient/user, or the alert can be sent after the healthcare practitioner approves the alert, or an alert can be sent solely manually by the healthcare practitioner.

Figure 20:
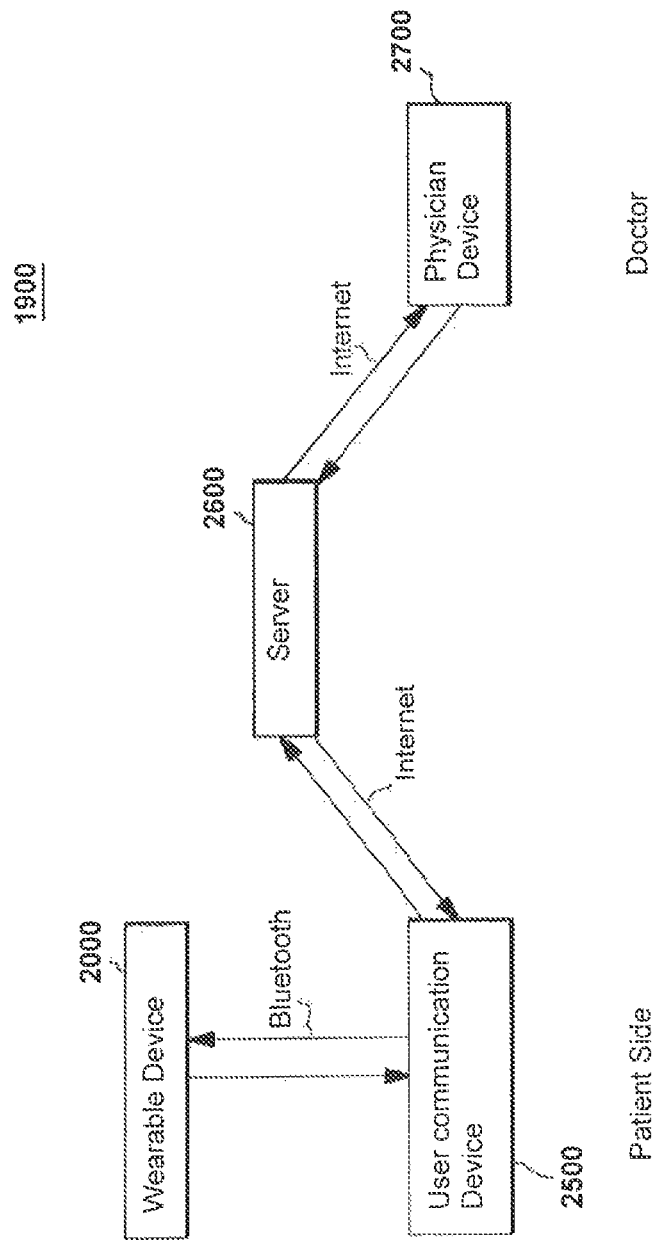
FIG. 20 is a schematic of system of detecting and treating abnormal cardiac function in accordance with an embodiment of the invention.

FIG. 20 is a schematic overview of a monitoring system 1900 in accordance with the invention. On the patient side, the patient is provided with portable wearable device 2000 that preferably continuously and automatically detects cardiac activity. One such portable wearable device is harness 2000 shown in FIGS. 21A-C and discussed below. Other to-be-developed portable wearable devices that monitor cardiac activity are also contemplated as being suitable for the purposes of the invention.

Sensor data is transmitted from wearable device/harness 2000 to the patient's communication device 2500 (e.g., a smartphone or similar device) via local, preferably wireless communication link, such as Bluetooth, near field communication (NFC), or similar existing or to-be-developed schemes. Sensor data includes a number of parameters, including but not limited to battery level of harness 2000, ECG data from one or more channels, accelerometer data from one or more channels, respiratory data, and the like. Smartphone 2500 can also send information to harness 2000. For example, smartphone 2500 can instruct harness 2000 to trigger an alert such as a vibration, sound, or thermal alert on the harness, or change how often the harness is sending data to the smartphone (every 30 seconds, every 1 second etc.), or the like. Additionally, if the embodiment of FIGS. 1-19 is included or incorporated into wearable device 2000, smartphone 2500 can instruct device 2000 to administer the appropriate amount of medication to the patient if required (e.g., because of a detected abnormality in cardiac activity, instructions pushed by the healthcare practitioner, preset time-dependent dosing, etc.). Also, if a serious cardiac event is detected, a message can be sent to harness 2000 from smartphone 2500 to stream the sensor data immediately and continuously as opposed to periodically for discrete amounts of time.

Smartphone 2500 sends all the sensor data it receives from harness 2000 to a remote server 2600 for the bulk of the analysis of the data. (The application running on smartphone 2500 can also perform at least some basic analysis of the data, however to prevent a significant drain on the battery of smartphone 2500, most of the analysis is performed remotely on a server or similar device.) The smartphone also sends any symptoms or activities that the patient entered on his smartphone. The smartphone may receive alerts from server 2600—these alerts may include messages the healthcare practitioner sends to the patient, or an abnormality in cardiac cardiac that server 2600 server detected based on the sensor data. As mentioned above, the alert may take the form of a request for information from the patient concerning a possible innocent explanation for the detected abnormality (e.g., elevated heart rate caused by exercise).

Server 2600 receives sensor data from smartphone 2500 and processes all the data to search for medical problems or to detect cardiac events. For example, server 2600 has read/write memory that includes a database having ranges for normal and abnormal values for various cardiac activity parameters, such as heart rate and amplitude, wave form shape, etc. Server 2600 compares the received ECG data to its database to determine if abnormal cardiac activity has been detected by wearable device 2000. Server 2600 processes all the data and also stores the data so the server can calculate long term trends for the patient.

Server 2600 makes the recorded ECG and its analysis available to the healthcare practitioner via the healthcare practitioner's device 2700. In one embodiment, server 2600 sends this information to website which a healthcare practitioner may access. In another embodiment, server 2600 pushes this information to the healthcare practitioner's device, either to a computer or similar device or to a communication device (e.g., smartphone). Regardless of the form of healthcare practitioner device 2700, the healthcare practitioner can access all of the processed patient's data, as well as any events or alerts that the server detected. Additionally, the healthcare practitioner can review any symptoms/activities that the patient entered on his smartphone. Moreover, the healthcare practitioner can send messages to the patient.

Figure 21A:
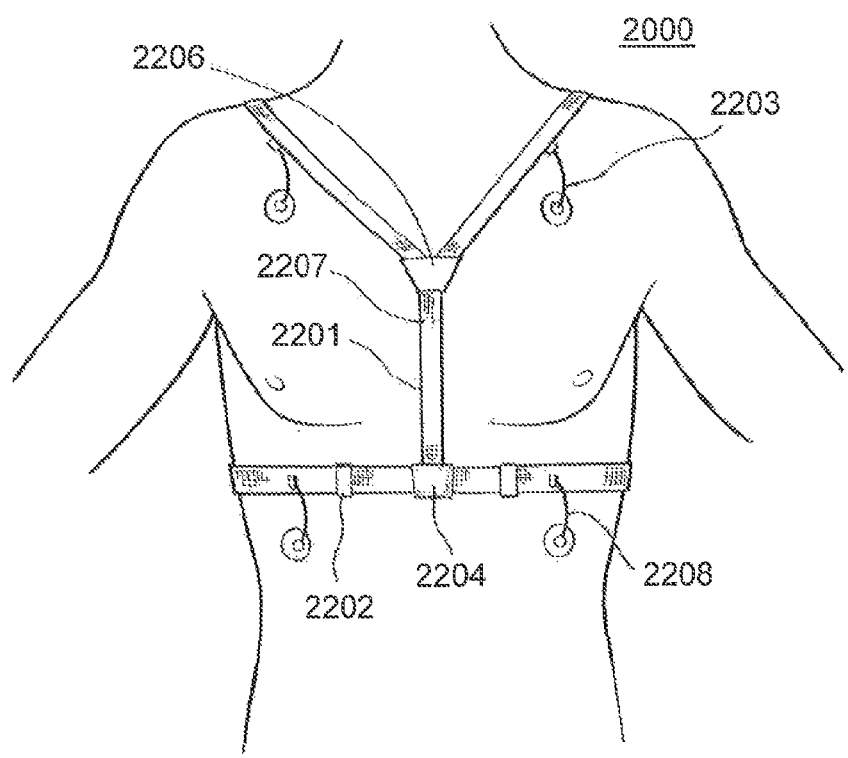
FIGS. 21A-D are schematics of a portable wearable device of the system of FIG. 20.
Figure 21B:
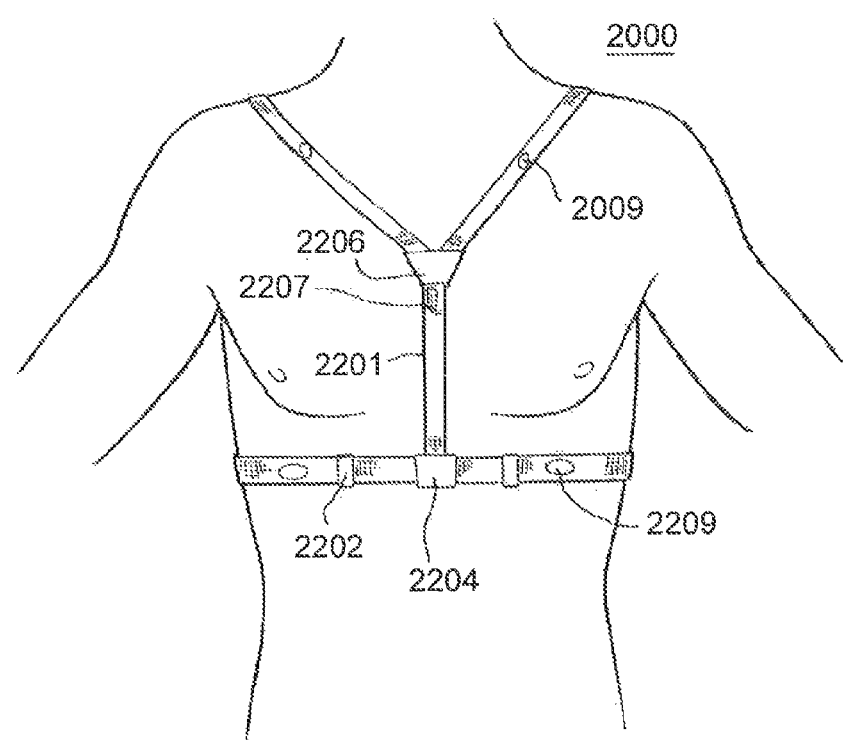
Figure 21C:
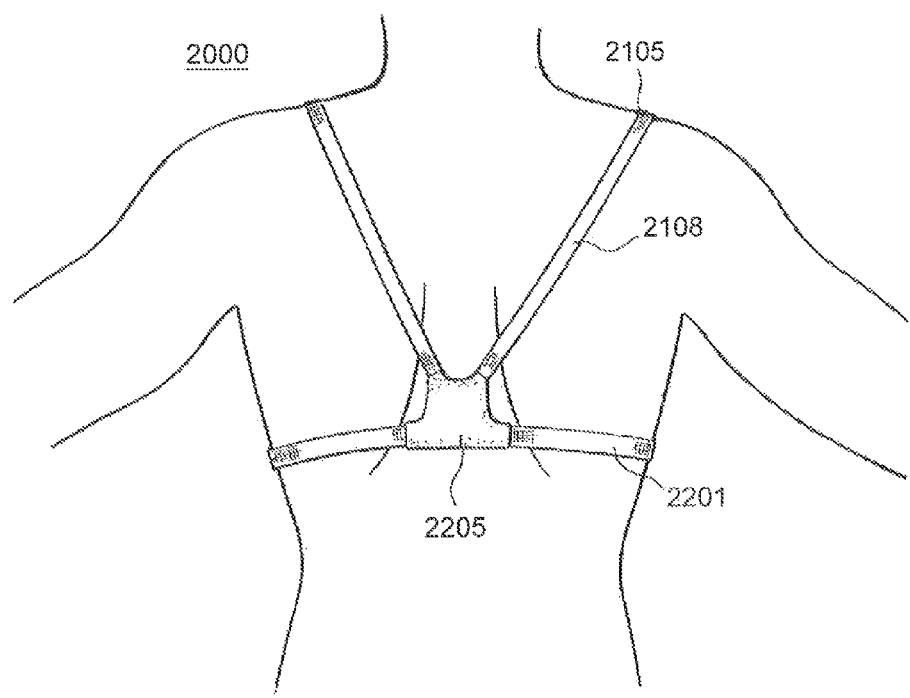
Figure 21D:
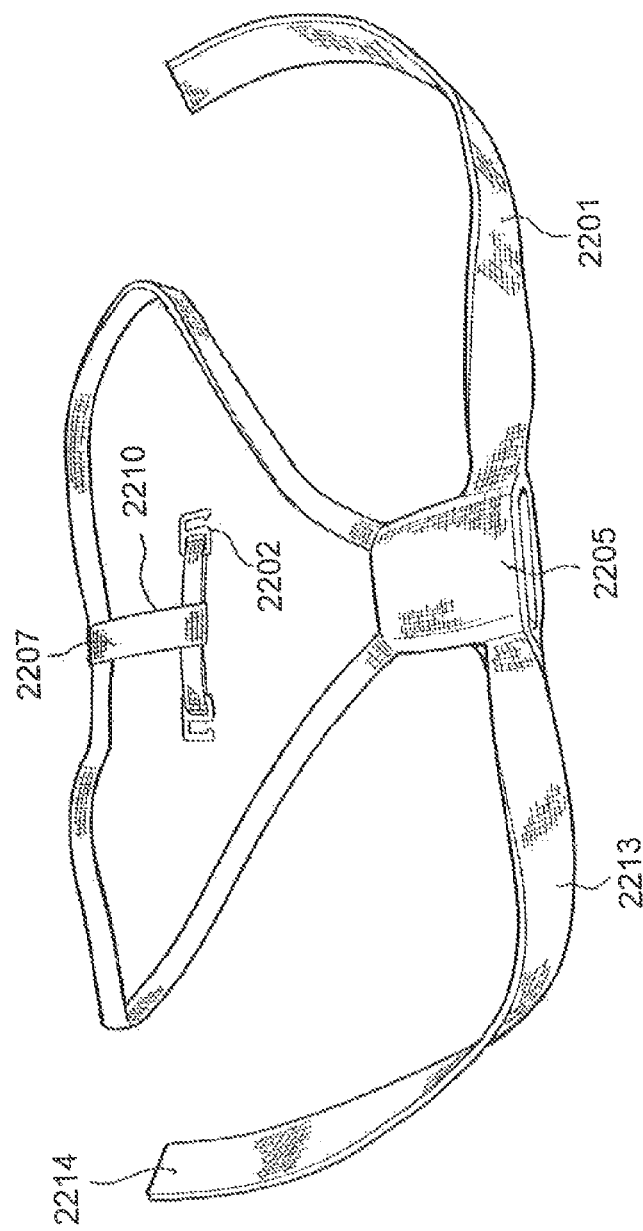

One embodiment of the user's wearable device 2000 is shown in FIGS. 21A-D as harness 2000. FIG. 21A schematically depicts a wet electrode version of harness 2000, FIG. 21B schematically depicts a dry electrode version of harness 2000, FIG. 21C schematically depicts the rear portion of harness 2000 suitable for either the wet or dry electrode version, and FIG. 21D schematically depicts the entire harness 2000 of the wet electrode variety.

Overall, harness 2000 is made from stretchy elastic material 2201 formed in various sections. As shown in cutaway 2108 of FIG. 21C, inside material 2201 is either conventional metal or elastic carbon "rubber" wire, the latter allowing for more elasticity of the device and thus more options for sizing, proper fitting, etc. Rubber housing 2205 encloses all of the electronics and power source (e.g., battery) of the device. Straps 2105 are adapted to fit over the user's shoulders.

Referring to the wet electrode harness of FIGS. 21A and D, harness sections 2202, 2204, 2207, and 2206 together make up a front inverted T strap 2210. The horizontal portion of T strap 2210 preferably ends in clasps 2202 (and/or any other fastening device or mechanism, e.g., snaps, buttons, hook and loop fasteners, etc.) that attach to ends 2214 of lateral strap 2213. The vertical portion of T strap 2210 preferably ends in clasp 2206 (or similar fastening device/mechanism) to connect T strap 2210 to shoulder straps 2105. T strap 2210 preferably comes in different sizes, so for different sized people, different T straps 2210 are provided. As an example, the main portion of harness 2000 may be provided in three sizes (e.g., Small, Medium, Large), and different-sized T straps may also be provided to the patient to obtain a perfect fit. It is less expensive to make different sized T straps 2210 for patients to swap out for their comfort than to make many different sized harnesses entirely, especially considering T strap 2210 need not include any wiring or electronics but can simply be elastic material. This way they get the best and most comfortable, and not tight fit. Lead wires 2203 and 2208 are attachable to conventional wet electrodes attachable to the user's torso. Lead wires 2203 and 2208 are preferably made relatively short so as to minimize the variations in the locations the electrodes may be disposed on the user's torso.

FIG. 21B depicts an alternate version of harness 2000 with like elements represented by like references numerals. Here, instead of lead wires 2203 and 2208 attachable to wet electrodes, dry electrodes 2209 are provided integrally with the straps of harness 2000. Instead of short wires coming out to connect to wet electrodes, the dry electrodes themselves are embedded underneath the elastic straps that the patient wears. This has the advantage of not requiring wet electrodes at all and enabling more consistent positioning of the electrodes simply by dint of donning the harness.

Figure 22:
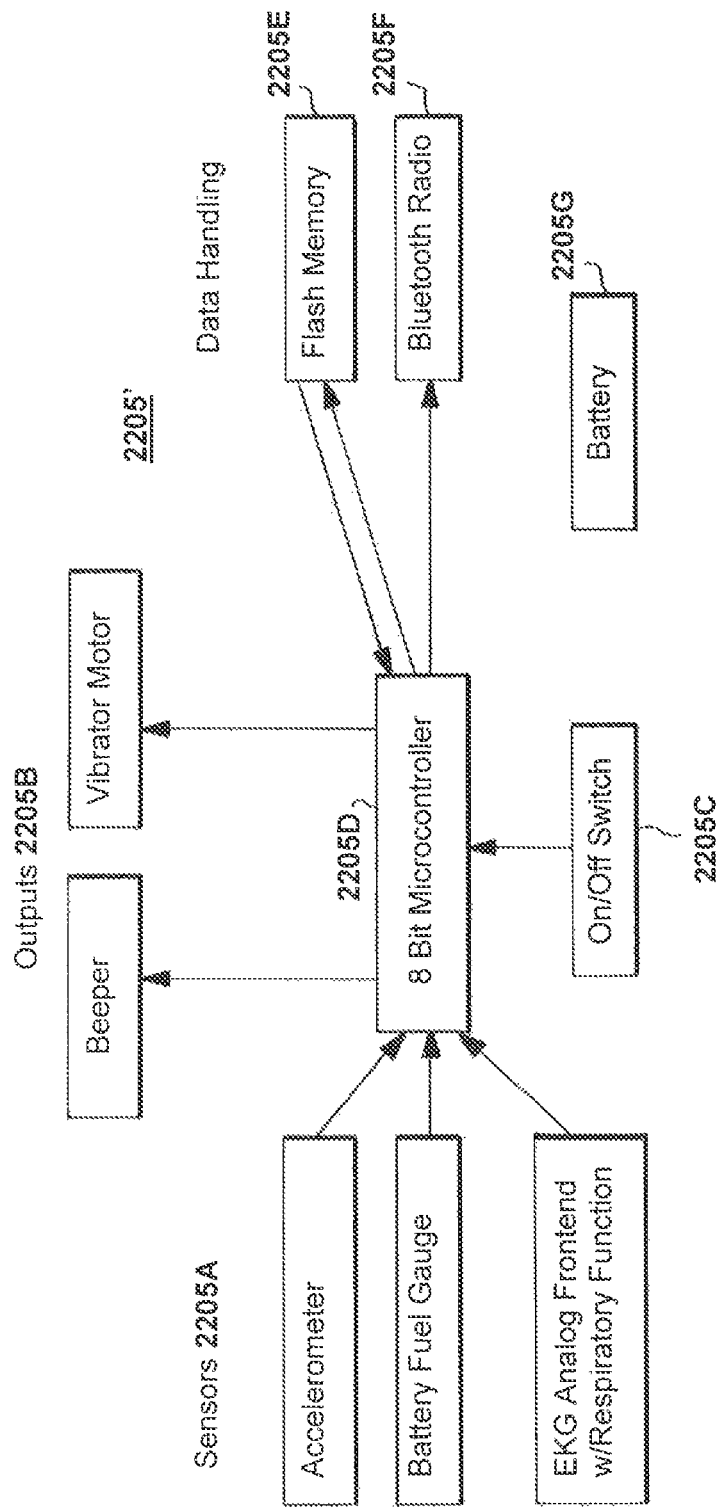
FIG. 22 is a schematic of the electronics of the portable wearable device of FIGS. 21A-D.

The specific electronics package 2205'contained in housing 2205 is depicted schematically in FIG. 22. Sensors 2205A detect movement, battery life, cardiac and respiratory function, and the like. The device boots up in a super low power mode. On/off switch 2205C wakes everything up and starts the main program. In one version, on/off switch 2205C is a pushbutton that the user depresses. Alternatively, in another version, the clasps of the harness 2000 are provided with electrical contacts so that simply closing the clasp of the harness closes the switch and wakes everything up.

Once everything is booted up, sensors 2205A detect movement, battery life, cardiac and pulmonary function, and other parameters. Microcontroller 2205D (e.g., an ATmega 1284P, or any equivalent thereof) starts recording values from the ECG frontend sensor (e.g., a TI ADS 1294R or any equivalent thereof). Data is preferably recorded at 250 Hz, possibly at 125 Hz; other data rates are also contemplated. In any event, microcontroller 2205D records the analog ECG and respiratory values on the flash memory 2205E. Microcontroller 2205D also preferably stores accelerometer data, preferably at a lower data rate, e.g., 50 Hz (which might be reduced to a low frequency as well). After it records enough time's worth of data (e.g., 30 seconds, or up to 3 hours), microcontroller 2205D sends out all the data that it recorded on memory 2205E to the user's communication device/smartphone 2500 via the Bluetooth module 2205F (e.g., an RN42 module, or any equivalent thereof). That is to say, electronics 2205' records a lot of data for a period of time (requiring relatively low power for a long time period) and then transmits all that data quickly via Bluetooth or similar local communication scheme (requiring high power over a short time period). As a result, battery life is optimized.

The accelerometer data is used to determine if the patient is moving around during an ECG reading. It gives context as to why heart rate might be high, why respiratory rate is high, etc. Additionally, because the accelerometer is a 3-axis sensor and it can readily be known in which direction gravity is pulling, using the accelerometer, it can be determined if the person is lying down or standing or substantially in any other position. This is useful because it can be determined what is occurring during sleep, which is relevant as many cardiac patients have sleep apnea.

Local outputs 2205B such as a beeper or vibrator may be provided onboard the electronics (inside the harness) to alert the patient. Alerts might be low battery warning (as detected by the battery fuel gauge that measures current battery level) or an alert triggered from the smartphone (e.g. dangerous heart rate alert or a timed medication dosing).

Electronics 2205' is powered via a rechargeable battery 2205G, preferably a lithium ion battery or the equivalent thereof.

As has been mentioned above, the wearable device 2000 transmits its data via local communication means to the user's communication device 2500, which then transmits the data to server 2600 and thence to the healthcare practitioner's device 2700. Server 2600 can also communicate analysis and healthcare practitioner information and messages back to communication device 2500. FIG. 23 depicts multiple screenshots of one embodiment of that interaction.

FIGS. 23A-F are screenshots of an application or "app" running on user device 2500. Multiple tabs at the bottom of each screen enable the user to navigate quickly amongst the various screens. Typical tabs include (as shown in FIGS. 23A-F) "home", "monitor", "alerts", and "settings." Other tabs may be provided in addition or in the alternative to these four, however an underlying design requirement is that the app be easy to use for a variety of patients who do not have either medical or software experience.

Figure 23B:
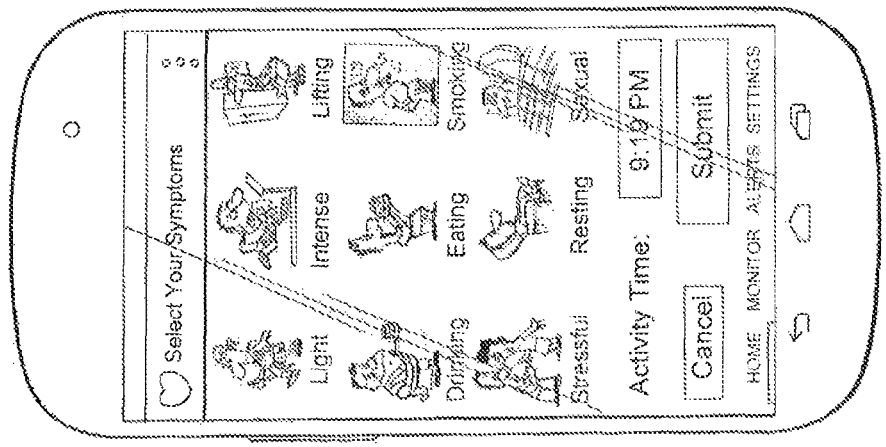
FIGS. 23A-F are exemplary screenshots of a user interface for the user communication device of FIG. 20.
Figure 23A:
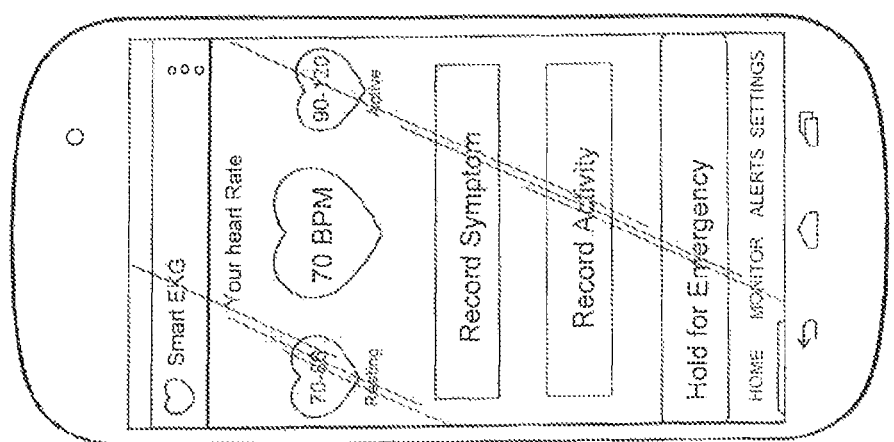

FIG. 23A depicts a screenshot of a home screen of the app on user device 2500. When the user opens it up, he sees his appropriate resting and active heart rates and his current heart rate. The user can choose to enter in Symptoms or Activities. An emergency button is also provided.

FIG. 23B depicts a screenshot of an activities screen. Here, the user can select what activities he is currently doing what he did earlier in time, or what he plans to do in the future. This information is sent to server 2600 to enable the correlation of patterns between heart events and activities, both for the specific patient and for global population demographics. Nine types of activities are depicted in FIG. 23B; the number may be more or fewer. Additionally, each type of activity may, when selected, call up one or more specific activities or enable quantification of the selected activity. For example, if the use selects "drinking", the app may query the user as to type and quantity of alcoholic beverages consumed. Similarly, if "intense" activity is selected, the app may offer the user sub-choices of different kinds of intense activity (running, swimming, skiing, etc.) and/or a duration of said activity. Other possibilities are also contemplated.

Figure 23D:
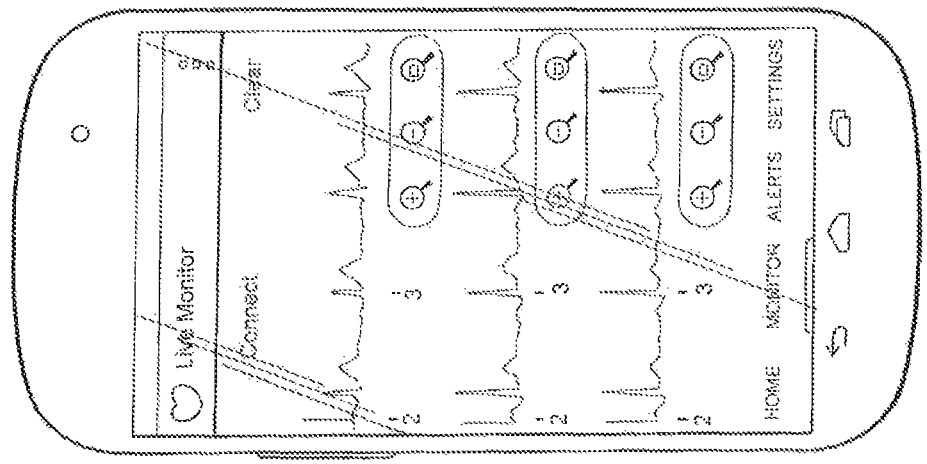
Figure 23C:
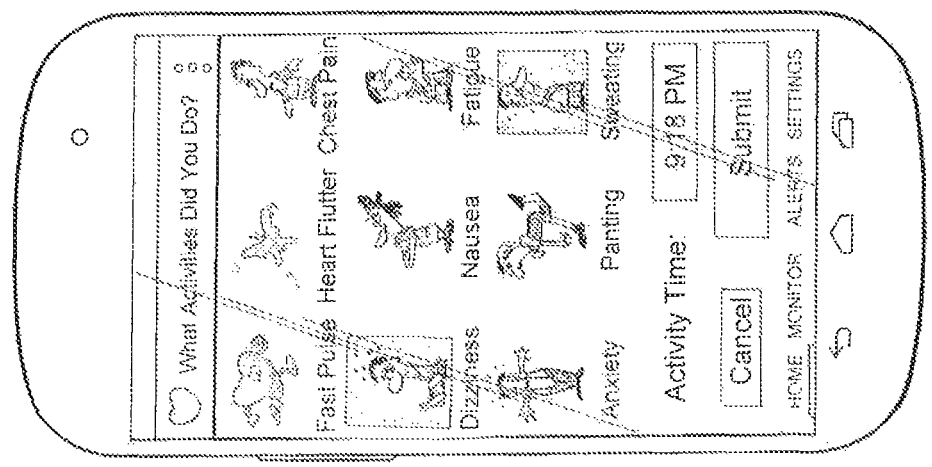

FIG. 23C depicts a screenshot of a symptoms screen. Here, the user is able to choose what symptom(s) he has, and that information is transmitted to server 2600 and stored along with the ECG.

FIG. 23D depicts a screenshot of an ECG screen. This screen falls under the "monitor" tab and shows an example of an ECG taken of the user's heart onscreen. The image may be static or dynamic, and it may be refreshable at a rate that optimizes the competing interests of battery life and providing data. One purpose of this screen is to reassure the user that the ECG is being read on harness 2000 and is being transmitted wirelessly to user device 2500. The ECG may show basic information like heart rate, how regular it is, and other heart rate qualities. Alternatively, the actual ECG may not be presented to users because it might confuse them or worry them.

FIG. 23E depicts a screenshot of an alerts screen on the user's device. Here, the user receives alerts on his device 2500 if it is detected that his ECG is abnormal/dangerous. As shown in the top portion of FIG. 23E, here the app is querying the user about the user's activity during an abnormal event, e.g., was the user exercising when an elevated heart rare was detected. The user also might get a reminder alert to take his medication, either at a predetermined time (e.g., an automatic reminder every day) or a reminder that would be prompted by a condition (e.g., take a heart-rate-lowering pill if heart rate is very high for an extended period of time).

FIG. 23F depicts a screenshot of an analysis screen on the user's device. Server 2600 sends this data to the app, where the patient can find patterns between heart conditions and symptoms/activities. This is so patients can see what they're doing wrong, and they understand and believe smoking is causing heart abnormalities/higher heart rate. As an example, it is one thing to lecture a patient that smoking is bad for his heart, it is quite another to point to specific smoking-related abnormal cardiac activity (e.g., tachycardia, as shown in FIG. 23F). This brings the user into the process so they are (hopefully) more compliant. A "personal notes" section may be provided for the user to enter notes into the system for viewing by the healthcare practitioner.

The "settings" tab enables app customization such as how often to send data to the server, enable/disable alerts, and the like.

Figure 23G:
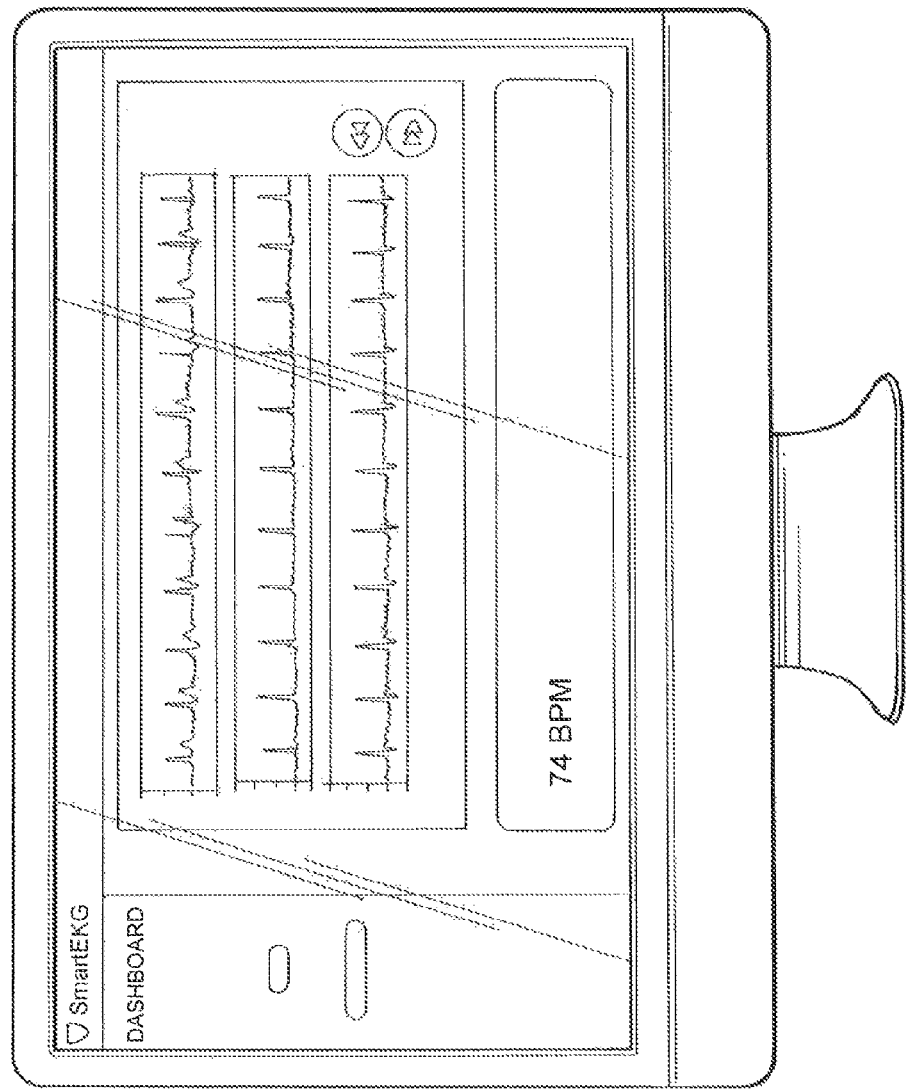
FIGS. 23G and H are exemplary screenshots of an interface for the physician device of FIG. 20.
Figure 23H:
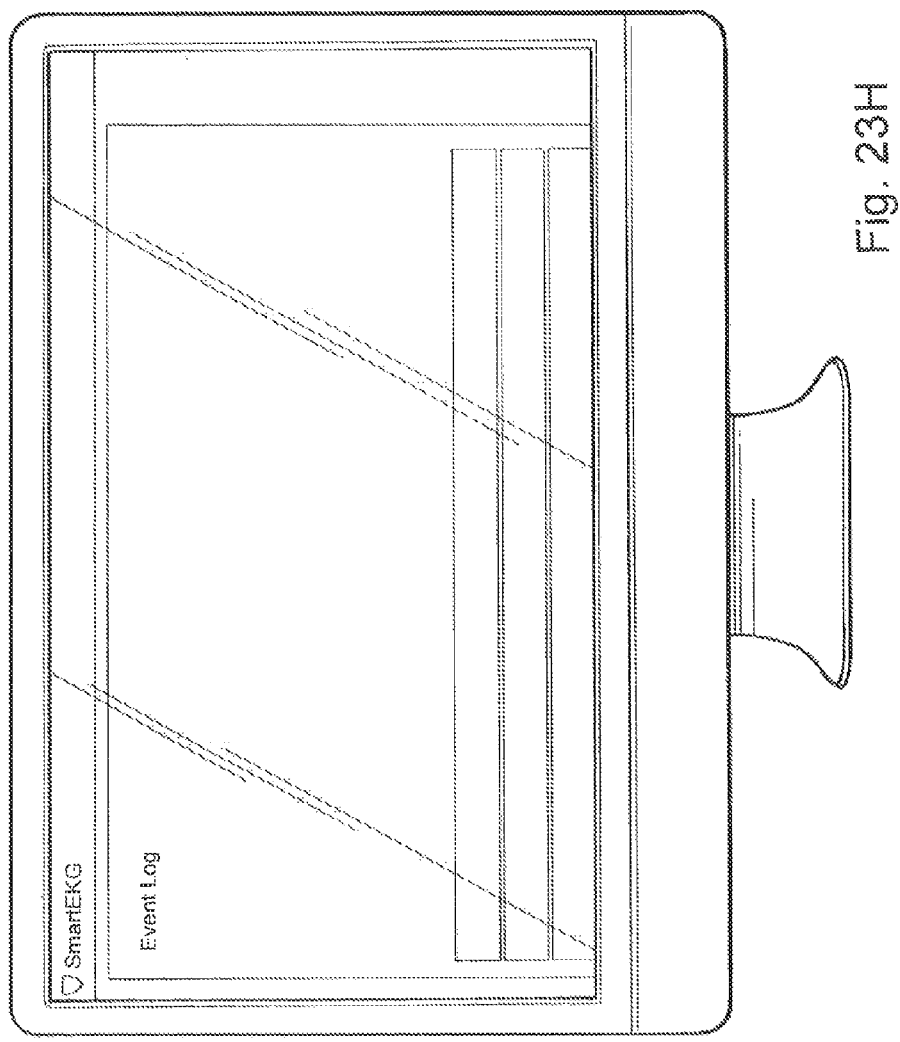

FIGS. 23G-H are screenshots of an app or software running on healthcare practitioner device 2700. These are what the doctor (or the like) will see when logging into the system and/or when the system pushes the information to the doctor in the event of a serious cardiac event.

FIG. 23G depicts a screenshot of an ECG transmitted to device 2700. The doctor gets this ECG that is wirelessly transmitted from the patient's device 2500 to server 2600. The doctor can read the ECG just as she would in her office or on paper and see abnormalities and the calculated heart rate along with any entry that the patient entered (symptom/activity) which gives him some context. Server 2600 cleans up and filters the ECG as well to make it visually nicer and cleaner (to be described below).

FIG. 23H depicts a screenshot of a warnings screen presented to the healthcare practitioner. The software looks for issues in the patient's ECG and generates warnings for the doctor to investigate. The doctor can then clear or flag warnings and look at the ECG (see FIG. 23G) to diagnose.

Figure 24:
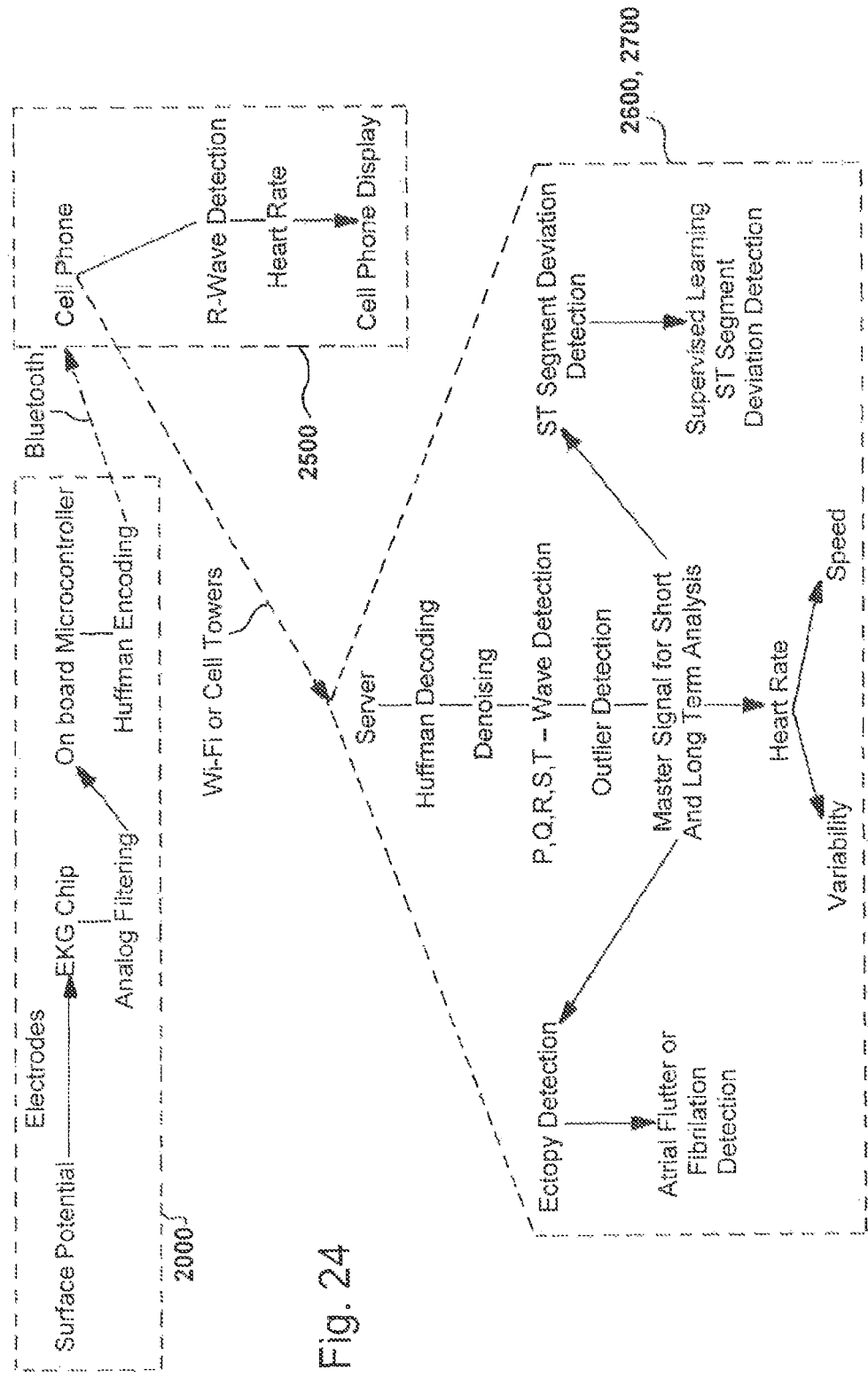
FIG. 24 is a schematic software flowchart depicting the acquisition and interpretation of cardiac activity in accordance with the invention.

Next, a description of the software and processes thereof of the invention is provided with reference to FIG. 24, a schematic flowchart depicting which of the elements of system 1900 typically perform which tasks. Typical computing languages in which the software may be written/compiled include, MATLAB, Octave, Python(x, y), and the like. The specific language is not as important as the functionality described herein. The flowchart of FIG. 24 joins the FIG. 9 code flowchart at the point indicated as "enact subroutines as fast as possible."

Long term monitoring data is a tricky data set. Since the patient is, by definition, in uncontrolled settings, the data can be corrupted by noise (random signal with a constant power density) and artifact (alteration in signal that misrepresents the underlying biophysical process). The analysis needs to be aware of these possibilities and reduce error with multiple fail safes and redundancies. The entire concept of processing monitor data can be divided into two domains: real time, and post processing. Real time means that the data is processed as quickly as possible as it is collected, whereas post processing has no such time constraints. As such, real time analysis is usually simplified, sacrificing accuracy and scope for the sake of speed. The invention is aware of such constraints and builds them into the model. The inventive system continuously updates itself, improving the longer the patient wears device 2000. It is preferred that a human healthcare practitioner check before any clinical action is undertaken.

Input. System data is collected by wearable device 2000 and starts with an ECG chip, for example, ADS 1294R by Texas Instruments. Its onboard analog filter does a significant part of the signal denoising. Before sending the data to the server, microcontroller 2205D (e.g., Atmega 1284p, an Atmel 8 bit chip) runs a Pan-Tompkins algorithm to detect R wave so as to give real time feedback on heart rate. Microcontroller 2205D then encodes the signal using, for example, Huffman encoding, with a dictionary premade from data recorded when the monitor was given. Server 2600 is provided with the same dictionary as wearable device 2000, unique for every person, and decodes the data. This encoding allows for extra security and signal compression.

The system then cleans the signal a bit more for two reasons: baseline shift, and artifacts.

Baseline shift. Although the signal should be zero centered, errors such as shifting electrodes can cause it to rise or fall. The two electrodes are in unique ion environments on the skin. The filter compares these two environments. If the environment of one changes without a symmetrical change in the other, this presents as a low frequency noise, a baseline shift. The gel electrodes compensate by covering a small area of the skin in electrolytic gel to get it to the all same potential. However, in embodiments using dry electrodes, it is more of a concern. The harness is tight to reduce (but not eliminate) risk of movement. By piece-wise detrending, the data the system can remove this shift. The system does this by lowpass filtering the data and then removing the linear fit of this new signal from the original every few heart beats.

Artifacts, lead off, noise, etc. Without an internal model of what the signal should look like, the analog filter cannot respond intelligently. The system decomposes the signal by projecting it onto an orthogonal basis (either a 4th order symlet or an eigenvector of the patient's own data) and only taking the first components. This allows the system to select only for data that "looks like" an ECG.

Feature Extraction

Among the more important portions of any ECG analysis is the feature extraction. The inventive system has two stages. The first is detection of the common graphical deflections. The Pan-Tompkins algorithm is first used to find the R wave peaks. The troughs of the Q and S waves are defined as the minimum within a certain distance of the R peak. To find the isoelectric voltage, a histogram of the signal is made between the T and P wave for every heartbeat, and the highest peak is selected to be the isoelectric voltage for that heartbeat. This is similar to taking the mode but allows for jitter. T waves are detected by taking the 10th order continuous wavelet transform of the segment after the S wave using a Gaussian wavelet. Extrema are noted by looking where this signal crossed the zero line. Then, the extremum with the largest absolute value away from the isoelectric line is noted to be the T wave peak. This allows for the detection of inverted and normal T waves. P wave detection is similar except that it is constrained to always be a positive deflection. Additionally, if the peak does not exceed noise level, then the algorithm returns a null value for its location. U waves may also be detected using the same methodology as T and P wave detection.

For the second stage, once these points are detected, any features that are desired can be extracted. What follows are some exemplary features that may be extracted, however any transformation of the ECG data can be used.

Heart Rate. If the heart rate ever rises above or falls below the preset limits (as defined by the doctor) for more than a certain number (e.g., three) heart beats, a warning is generated.

Ectopy. The ratio of R-R intervals for each heartbeat is calculated. If there is a small ratio followed by a large ratio then that middle beat was ectopic.

Atrial Fibrillation Detection. To detect atrial fibrillation a few separate variables are used. First and simplest, the heart rate is used. However, there are many possibilities for supraventricular tachycardia, so it cannot be used alone. The system also uses heart rate variability, defined as the 1st and 2nd derivative of the heart rate. Lack of a P wave presence is hard to prove, since it could be that the system simply missed the detection. Therefore, the system uses variation in height and locale of P wave, as inconsistencies indicate an unstable system. Last but not least the Shannon entropy of the signal between the S wave of that heartbeat and the Q wave of the next heartbeat is calculated. To train the classifier, standard data from the MIT arrhythmia database is preferably used, as patient presentation of these variables in the case of Atrial fibrillation is very similar.

To prevent ectopy from biasing the data, any episodes of ectopy were replaced with the average heart beat in that region.

ST Deviation Detection. The system utilizes a dual approach. First, the system uses the standard method of comparing the J point to the isoelectric line. To avoid basic noise errors, the system averages across multiple heartbeats. Once there is a confirmed episode, the system uses all of those heartbeats to train the Naïve Bayesian Classifier and use it as the primary detector. For each heartbeat, the portion of the signal from the trough of S to the peak of T is extended to the same large number of samples via a low pass filter using a Kaiser window. Then, the principle components are extracted, using the coefficients from the Principle Component Analysis performed on the training set. The first few components (composing ~90% of the variability) are used to classify the heartbeats.

Classification. While there are many methods for classifying features, the inventive system preferably uses a Naïve Bayesian Classifier when there is a training dataset. In MATLAB, for example, the classifier may be from the PRT toolbox, and in Python(x, y) it may preferably be from the Scikit toolbox.

Since any method is susceptible to error, the output of the classifier was convolved with a Gaussian and a threshold was set. This way, the system detects "events" spanning multiple heart beats. Additionally, where possible, there should be confirmation from multiple leads.

Long Term Tracking While all of these classifications are important in the short term, they also are significant in the long term. All of the data is stored and personal reports can be generated on command. For example, the doctor can query the database for the total time spent in fibrillation last month, or the average heartbeat last week, or the like. One important metric is the Total Ischemic Burden. A representative of primary and secondary ischemic strain on heart muscle, it is the total time spent in ST elevation of depression, weighted by the severity during that time.

Respiratory Rate. As an option, the user or physician may decide to measure the resistance across the lungs. Taken as a continuous signal, peak detection allows the algorithm to provide a respiratory rate. Additionally, given the same conditions, long term analysis allows for detection of pulmonary effusions or edema by comparing the base resistance over time. Additionally, any interruptions in breathing patterns (such as those brought on by sleep apnea) can be noted for further analysis.

The bulk of the signal processing described above occurs on server 2600 so as to save the battery power of user device 2500. However, it is shown in FIG. 24 as being performed optionally also on physician's device 2700.

Having described certain embodiments of the invention, it should be understood that the invention is not limited to the above description or the attached exemplary drawings. Rather, the scope of the invention is defined by the claims appearing hereinbelow and includes any equivalents thereof as would be appreciated by one of ordinary skill in the art.

What is claimed is:

1. A method for detecting and treating abnormal cardiac function in a mammalian patient, the method comprising:
   monitoring a mammalian patient's cardiac activity via a portable wearable device having electrodes and a microcontroller in communication with the electrodes;
   remotely detecting features in the cardiac activity indicative of abnormal cardiac function;
   in response to detection of an abnormal cardiac function, alerting at least one person of the detected abnormal cardiac function of the patient including the patient via the patient's mobile phone and alerting a remote healthcare practitioner via local connection between the portable wearable device and the patient's mobile phone;
   in response to detecting abnormal cardiac function, requesting data from the mammalian's patient concerning ordinary patient activity that corresponds to the detected abnormal cardiac function; and
   in response to a receipt of instructions from the remote health care provider, causing to be administered, at least one medication corresponding to the detected abnormal cardiac function.

2. The method of claim 1, wherein in the case of abnormal heart rate, said alerting comprises alerting the patient on the patient's mobile phone via local a connection between the patient's portable wearable device and the patient's mobile phone.

3. The method of claim 1, wherein the patient is human and wherein said medication administration comprises alerting the patient to self-administer the at least one medication.

4. The method of claim 3, wherein the alerting the patient comprises at least one of: i) sending a message to the patient's mobile phone; or ii) causing the portable wearable device to emit a human-perceivable message.

5. The method of claim 4, wherein the human-perceivable message comprises at least one of a sound, a light, a vibration, or a change in temperature of an element of the portable wearable device.

6. The method of claim 1, wherein the patient is non-human and wherein the medication administration comprises alerting a nearby human to administer the at least one medication to the patient.

7. The method of claim 1, wherein said alerting a nearby human further comprises at least one of: i) sending a message to a mobile phone of the nearby human; or ii) causing the portable wearable device to emit a human-perceivable message.

8. The method of claim 1, wherein the medication administration comprises administering the at least one medication via the portable wearable device.

9. The method of claim 1, wherein the remote monitoring further comprises attaching electrodes to the patient, detecting cardiac activity via the electrodes, creating signals corresponding to the detected cardiac activity, said signals enabling identification of at least one detectable cardiac parameter, and sending the signals to a remote computer for comparison of a value of the detectable cardiac parameter to a range of normal values for the cardiac parameter.

10. The method of claim 9, wherein the signal sending further comprises sending the signals from the portable wearable device to a remote computer server via the patient's mobile phone.

11. A system for detecting and treating abnormal cardiac function in a mammalian patient, the system comprising:
   a portable wearable device having a plurality of electrodes adherable to the patient's body, said electrodes sensing cardiac activity and creating signals corresponding to the sensed cardiac activity; a microcontroller in communication with said electrodes, adapted to receive said sensed cardiac activity signals and create digital signals enabling identification of at least one cardiac parameter;
   a remote computer server having read/write memory in communication with said portable wearable device, said server adapted to compare values of said identified at least one cardiac parameter with a range of normal values for said at least one cardiac parameter stored in said read/write memory; and
   a user interface, residing on the patient's mobile phone and adapted to enable communication between the portable wearable device and the remote computer server and to receive analysis of the identified at least one cardiac parameter by said remote computer server in response to a receipt of instructions from the remote health care provider,
   wherein the portable wearing device causes to be administered, at least one medication corresponding to the detected abnormal cardiac function in response to a receipt of instructions from the remote health care provider, and
   wherein said portable wearable device further comprises a medication dispensing module having a dispensing mechanism and a quantity of at least one medication, wherein when said remote computer server determines that said identified at least one cardiac parameter is not within a normal range, said remote computer server communicates an instruction to said portable wearable device to dispense a dose of said medication.

12. The system of claim 11, wherein the user interface is adapted to accept user-enterable information and communicate said user-enterable information to said remote computer server.

13. The system of claim 11, said at least one cardiac parameter comprising at least one of P, Q, R, S, T, and U waves, ST segments, Heart Rate Variability, T wave inversion heart rate, regularity, atrial fibrillation, premature ventricular contractions, premature atrial contractions, and premature junctional contractions.

14. The system of claim 11, further comprising a practitioner interface, residing on a healthcare practitioner's device in communication with said remote computer server, adapted to enable a healthcare practitioner to review said identified at least one cardiac parameter.

* * * * *